United States Patent [19]

Martin et al.

[11] Patent Number: 5,577,837
[45] Date of Patent: Nov. 26, 1996

[54] TEMPERATURE CONTROLLED HEPA-FILTERED CONSOLE SHAKER

[75] Inventors: Paul M. Martin, Cutler; Gregory J. Graham, Marietta; David S. Farrar, Marietta; Stephen R. Faigley, Marietta, all of Ohio

[73] Assignee: Forma Scientific, Inc., Marietta, Ohio

[21] Appl. No.: 445,013

[22] Filed: May 19, 1995

[51] Int. Cl.⁶ .............................. B01F 11/00; B01F 15/06
[52] U.S. Cl. .......................... 366/145; 366/147; 366/208
[58] Field of Search ..................................... 366/110, 111, 366/112, 114, 145, 146, 147, 208, 209, 213, 214, 219

[56] References Cited

U.S. PATENT DOCUMENTS

| | | |
|---|---|---|
| Re. 29,880 | 1/1979 | Duff. |
| Re. 30,730 | 9/1981 | Duff. |
| 3,472,493 | 10/1969 | Blank et al. ............................ 366/112 |
| 3,601,372 | 8/1971 | Harmes, III ......................... 366/147 X |
| 3,634,651 | 1/1972 | Siegel et al.. |
| 3,944,188 | 3/1976 | Parker et al. ....................... 366/145 X |
| 4,045,179 | 8/1977 | Bunce. |
| 4,054,416 | 10/1977 | Duff. |
| 4,482,367 | 11/1984 | Howeth. |
| 4,679,615 | 7/1987 | Livne. |
| 4,747,693 | 5/1988 | Kahl ......................................... 366/208 |
| 4,907,893 | 3/1990 | Niemeck et al.. |
| 4,943,164 | 7/1990 | Ohishi et al. ....................... 366/110 X |
| 5,052,812 | 10/1991 | Tannenbaum et al. ............ 366/145 X |
| 5,060,151 | 10/1991 | Mikyska et al. ................... 366/208 X |
| 5,090,617 | 2/1992 | Swan et al.. |
| 5,114,583 | 5/1992 | Concin. |
| 5,149,654 | 9/1992 | Gross et al.. |
| 5,264,129 | 11/1993 | Simpson et al.. |

FOREIGN PATENT DOCUMENTS

| | | | |
|---|---|---|---|
| 303027 | 2/1989 | European Pat. Off. ............... | 366/114 |

*Primary Examiner*—Charles E. Cooley

[57] ABSTRACT

A console shaker which includes a shaker device mounted within a temperature and lighting controlled chamber and an air jacket which completely surrounds the chamber and also provides substantially laminar, HEPA-filtered air flow through the chamber in one direction. A refrigeration device and a heating device either cool or heat the air before it flows through the HEPA filter. The HEPA filter is mounted at the end of the chamber which defines an air inlet to the work chamber and an outlet is disposed at the opposite end of the chamber. The outlet end of the chamber receives air from both within the workspace of the chamber as well as from the front and rear air spaces of the air jacket. A microprocessor based control system provides an interface between the user and the various components for establishing the conditions within the chamber, such as shaker speed, temperature, time and lighting to be controlled by the user. To allow quick setting of the overall conditions or control parameters, the microprocessor based system allows one of a plurality of preset programs to be chosen by the user to set shaker speed, chamber temperature and time.

62 Claims, 12 Drawing Sheets

Microfiche Appendix Included
(2 Microfiche, 117 Pages)

| | |
|---|---|
| SKIP_1S_TSK | If one second interval, clear flag; else skip 4 tasks |
| UPDATE-RUNTIME | Update current runtime by one second |
| ALM-TIME-TSK | Decrement time alarm counters |
| RTN-DISP-TSK | Return to main display if no activity for five minutes |
| LHT-TIME-TSK | Update light timer; change state of light if needed |
| | |
| SKIP-5S-TSK | If five second interval, clear flag; else skip 20 tasks |
| MTEMP?-TSK | If no temperature controller, skip 13 tasks |
| RD-MTEMP | Read main temperature sensor from A/D |
| SHTDN-A/D | Tri-state A/D output |
| LIN-MTEMP | Linearize main temperature sensor reading |
| CHK-M-T-SNSR | Compare reading for out-of-range fault |
| RD-OTEMP | Read over temperature sensor from A/D |
| SHTDN-A/D | Tri-state A/D output |
| LIN-OTEMP | Linearize over temperature sensor reading |
| CHK-O-T-SNSR | Compare reading for out-of-range fault |
| HEAT-TSK | If temperature controller disabled, skip 4 tasks |
| MTEMP-PID-TSK | Use P-I-D control to activate heater, compressor |
| CHK-TEMP-HI-ALM | Compare temperature reading to set point + tracking limit, enable alarm and disable heater if appropriate |
| CHK-TEMP-LO-ALM | Compare temperature reading to set point - tracking limit, enable alarm and disable compressor if appropriate |
| TEMP-AVG-TSK | Average recent main temperature readings for display |
| UPDATE-RPM | Send RPM set point to motor controller, read RPM |
| CHK-RPM-HI-ALM | Compare current RPM to set point + tracking limit, enable alarm and disable motor if appropriate |
| CHK-RPM-LO-ALM | Compare current RPM to set point - tracking limit, enable alarm and disable motor if appropriate |
| ALM-DISP-TSK | Insert next alarm message into queue for UPDATE_LCD |
| PRINT-TSK | Print current status on RS-232/485 output if enabled and one-hour timer has expired |
| PRINTI-TSK | Print diagnostics if enabled and time interval expired |
| ANNUNC-TSK | Sound speaker if appropriate |
| REM-ALM-TSK | Activiate remote alarm relay if appropriate |
| CHK-RESET-MSG | Add reset message into queue for UPDATE_LCD if any alarm is active; remove reset message from queue if no alarms are active |
| CHK-OT-ALM | Check hardware overtemperature alarm; enable alarm and disable heater if appropriate |
| CHK-UT-ALM | Check hardware undertemperature alarm; enable and disable compressor if appropriate |
| LID-SWTCH-TSK | If lid is opened, halt motor and blower |
| VIS-ALM-TSK | If alarm, enable LED flash |

FIG. 8

TEMPERATURE CONTROLLED HEPA-FILTERED CONSOLE SHAKER

REFERENCE TO MICROFICHE APPENDIX

A microfiche appendix with two microfiche and 117 frames is attached to this application. This appendix is subject to copyright protection. The copyright owner has no objection to copying of the appendix in the form in which it appears in the files of the United States Patent Office, but reserves all other rights under copyright law.

FIELD OF THE INVENTION

The present invention generally relates to apparatus used in the production and growth of biological cultures and, more specifically, to apparatus for producing conditions which promote and speed the production and growth of such cultures.

BACKGROUND OF THE INVENTION

It is generally known that to produce and grow biological cultures and to effectively complete photosynthesis studies, for example, it is desirable to control and optimize various factors. These factors include the interaction between the liquid culture media and the surrounding gaseous environment as well as the temperature and lighting conditions in the environment of the culture media. For the purpose of increasing the exchange of gas with the liquid culture specimen, shaking and stirring devices are used to increase the interaction of the growth medium to the surrounding gaseous environment.

Shaking or stirring the culture medium stops short in many applications and studies of producing conditions which are most ideal. Temperature uniformity in the environment of the culture medium is also a key factor in many applications and studies. Deviations in the temperature may have adverse effects on the desired growth of the culture medium or may adversely affect the reliability of study results.

Various chambers or workspaces have been developed which provide some means for maintaining a more constant or uniform temperature within the environment containing the growth cultures. These methods include providing a water jacket or strip heaters in the walls surrounding an incubator or growth chamber. However, these methods have various drawbacks and limitations including, in the case of a water jacket incubator, the relative complexity and high cost associated therewith and, in the case of the heated wall or "warm wall" incubator, not only the manufacturing and maintenance expense but the inability to adapt this type of device to an application requiring refrigeration of the culture medium.

Another general disadvantage of past devices for optimizing the parameters associated with culture growth involves the difficulty of setting all of the various conditions quickly and accurately for any given application or study. If shaker mechanisms or other stirring devices are used in a temperature controlled environment by a scientist or technician, the shaker or stirring device is controlled separately from environmental controls such as the lighting and temperature.

Finally, contamination of the culture specimens either from the ambient environment or from cross contamination between culture specimens has been a continuing problem. Various methods for preventing such contamination have been proposed and developed, such as in the area of biological safety cabinets which employ high efficiency particulate air or "HEPA" filters. Again, however, such safety cabinets are adequate for many applications but are not quickly and easily adapted for use in those applications and studies which further require precise temperature control and temperature uniformity, shaking and stirring of the culture medium and easy lighting control. Specifically, none of the known devices in this area can provide quick and precise control of all of these parameters in a relatively low cost manner. It would therefore be desirable to provide a relatively low cost apparatus which allows a combination of the above parameters to be controlled in a quick, easy manner.

SUMMARY OF THE INVENTION

To this end, the present invention provides a console shaker which, in one aspect, includes a shaker device mounted within a temperature and lighting controlled chamber and an air jacket which completely surrounds the chamber to provide an insulative effect to said chamber and also provides substantially laminar, filtered air flow through the chamber in one direction. At one end of the air jacket a high efficiency particulate air (HEPA) filter is mounted to filter the air flowing through the chamber. Temperature regulating units are disposed within the base of the unit and preferably include both a refrigeration unit and a heating unit which, depending on the application needs, either cool or heat the air before it flows into the air jacket and through the HEPA filter into the chamber. The HEPA filter is mounted at the end of the chamber which defines an air inlet to the work chamber and an outlet is disposed at the opposite end of the chamber. The outlet end of the chamber receives air from both within the workspace of the chamber as well as from the front and rear air spaces of the air jacket. The console shaker includes an upwardly opening lid for selectively sealing and providing access to the workspace or chamber.

As air flows through the chamber in a single direction by first passing through the HEPA filter, contamination of the specimens within the chamber is prevented not only by the filter itself but by the resulting laminar flow through the chamber. Air is simultaneously directed through the air jacket or air plenums which preferably surround the chamber on four sides and the bottom thereof. Combined with an outer insulated wall of the console shaker, the heated or cooled air jacket serves as a close approximation of an isothermal wall condition about the chamber. With this system, temperature may be controlled within ±0.1° C. and temperature uniformity is ±0.2° C.

Another key feature of the present invention is the ability, through a microprocessor based system, to provide for an easy interface between the user and the various components for establishing the conditions within the chamber, such as shaker speed, temperature, time and lighting to be controlled by the user. In this regard, through a simple keypad and display on the outside of the console shaker, time, temperature, shaking or stirring speed, and lighting conditions may be quickly set to the desired overall condition appropriate for the application or study. To allow even quicker setting of the overall conditions or control parameters, the microprocessor based system allows one of a plurality of preset programs to be chosen by the user. Each program will store desired values for some or all of the above-mentioned parameters and control the various necessary components upon selection of the program and activation of the apparatus from the keypad.

Other unique aspects of the programmable control include the ability of the various keys or push buttons on the keypad to be reassigned functions in accordance with the various parameters to be set, such as time, temperature and shaker speed. This allows a very simple keypad and display to be used having a small number of push buttons which do not take up a substantial amount of space on the outside of the console. A calibration feature is also provided which allows the user to re-calibrate both the motor speed of the shaker apparatus as well as the temperature within the workspace or chamber directly from the keypad. Various other advantageous features of the control include the ability to remotely monitor the status of the shaker and various alarm conditions, an access code used to prevent unauthorized reconfiguration, among others.

Other objects and advantages of the present invention will become more readily apparent to those of ordinary skill in the art upon review of the following detailed description of a preferred embodiment taken in conjunction with the accompanying drawings.

BRIEF DESCRIPTION OF THE DRAWINGS

FIG. 8 is a listing of the tasks performed by the TASKER step 302 of the main program loop of FIG. 7;

DETAILED DESCRIPTION OF THE PREFERRED EMBODIMENT

The Console Shaker

Figure 1:
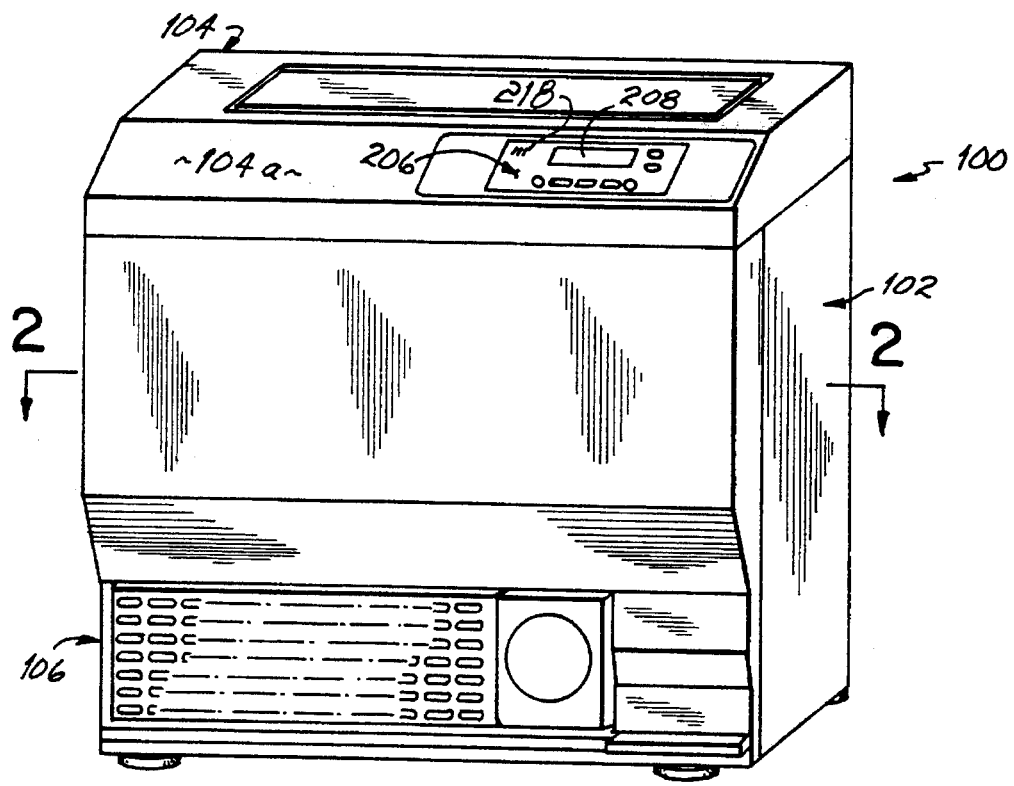
FIG. 1 is a perspective view of a console shaker apparatus constructed in accordance with the present invention.

Referring first to FIG. 1 in general, a console shaker 100 is shown and includes a chamber or workspace section 102, an upper hinged lid 104 and a lower base portion 106 which preferably contains both a refrigeration or air conditioning unit and a heating unit as will be described further below. A front angled surface 104a of lid 104 includes a keypad 206 having a display 208 for allowing the user to easily control the operation of console shaker 100 through a microprocessor control system which will be described in detail below.

Figure 2:
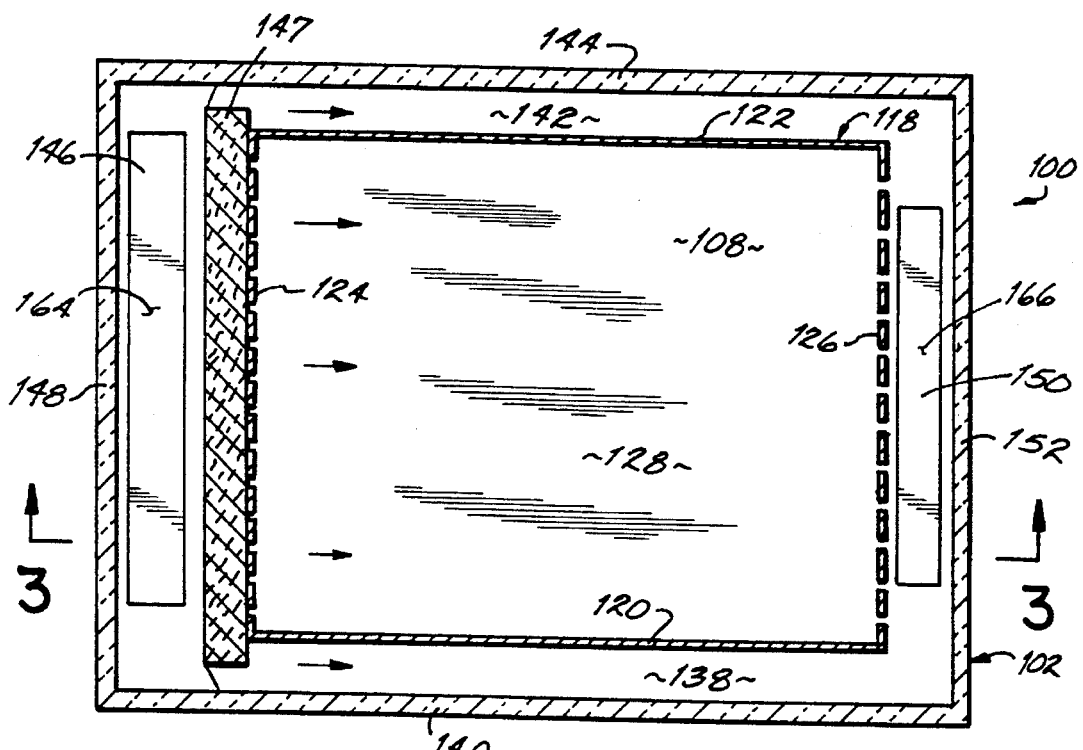
FIG. 2 is a cross-sectional view taken along line 2—2 of FIG. 1.
Figure 3:
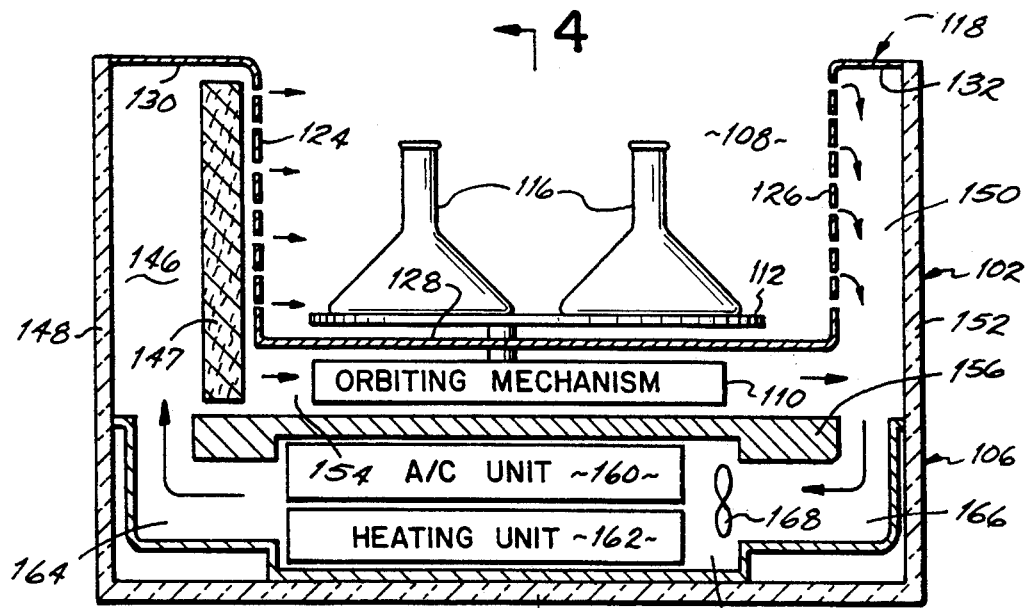
FIG. 3 is a cross-sectional view of the console shaker shown in FIG. 1 and taken line 3—3 of FIG. 2.
Figure 4:
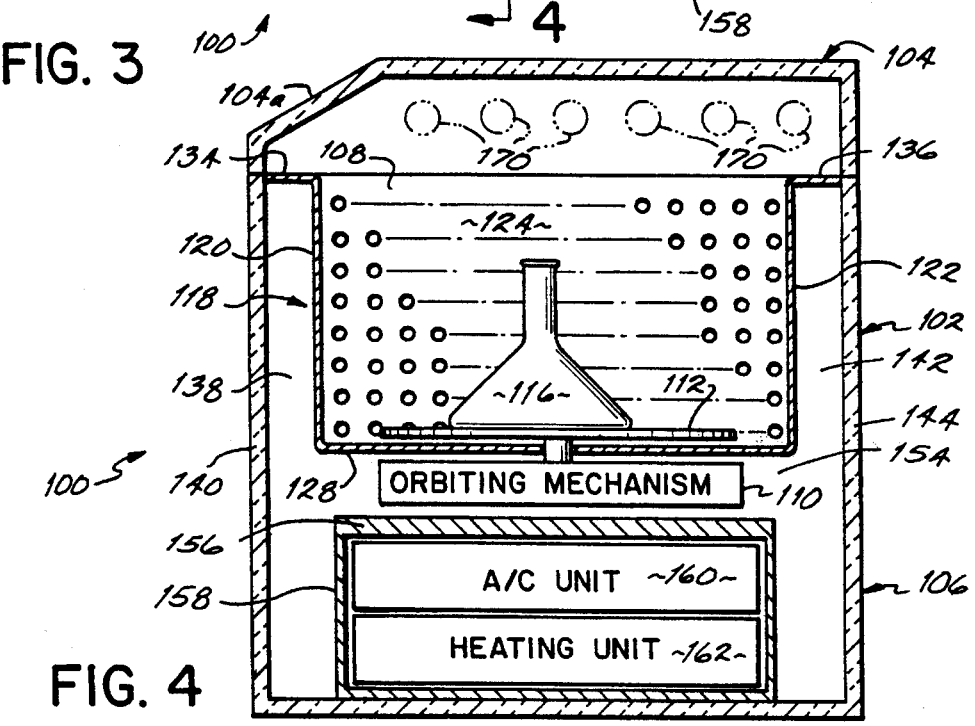
FIG. 4 is a cross-sectional view of the console shaker illustrated in FIG. 1 and generally taken along line 4—4 of FIG. 3.

Referring now to FIGS. 2–4, chamber or workspace section 102 of console shaker 100 includes an inner workspace or chamber 108. The platform 112 of an orbital shaker mechanism 110 is located at the bottom of chamber 108, however, the remaining drive components, etc., thereof are located below chamber 108. Orbital shaker mechanism 110, for example, may be of the type disclosed in co-pending and commonly assigned U.S. patent application No. 08/444,658, filed concurrently herewith. Flasks or other vessels 116 of various liquids, such as biological culture media, may be mounted on platform 112 in a known manner.

In accordance with one aspect of this invention, an air jacket insert 118 is provided within chamber section 102 and includes a front insert wall 120, a rear insert wall 122, a pair of perforated end walls 124, 126 and a bottom insert wall 128 which together generally define workspace or chamber 108. To further contain and enclose the air jacket which is thereby formed and which will be described below, air jacket insert 118 also includes a pair of end top walls 130, 132, as shown in FIG. 3, as well as a pair of side top walls 134, 136 as shown in FIG. 4. Air jacket insert 118 is preferably formed from a thin metal sheet material such as stainless steel. A front air plenum 138 is thereby formed between front insert wall 120 and a front insulated outside wall of console shaker 100. A rear air plenum 142 is formed between rear insert wall 122 and rear insulated outside wall of console shaker 100. An air plenum 146 which is used as an air supply plenum is formed between end insert wall 124 and outside insulated wall 148 of console shaker 100. Air supply plenum 146 includes a high efficiency particulate air (HEPA) filter 147 generally disposed against perforated insert wall 124 as shown in FIGS. 2 and 3. A return air plenum 150 is formed at the opposite end of console shaker 100 between perforated end insert wall 126 and insulated outside wall 152 of console shaker 100. Finally, a bottom air plenum 154 is provided generally between bottom insert wall 128 and a partition 156 which is spaced from bottom insert wall 128 and which separates bottom plenum 154 and a lower temperature control compartment 158 contained in base 106 of console shaker 100.

Referring to FIGS. 3 and 4 in particular, temperature control compartment 158 contains both an air conditioning or refrigeration unit 160 and a heating unit 162 for optionally cooling or heating air which is directed into workspace or chamber 108. Air conditioning unit 160 may be comprised of conventional refrigeration components, such as a condenser, a compressor, an evaporator and an expansion device, while heating unit 162 may utilize conventional electrical resistance type heating elements. Units 160 and 162 are controlled in a manner to be described in detail below. In this regard, air paths 164, 166 respectively connect temperature control compartment 158 to supply plenum 146 and return air plenum 150. A fan 168, schematically shown in FIG. 3, provides a means for moving air through console shaker 100 in the manner shown by the arrows in FIGS. 2 and 3 and as will be described below. Finally, a plurality of florescent lights 170 are mounted within lid 104 directly above workspace or chamber 108 for optionally providing light therein, for instance, in the case of simulating day and night conditions for photosynthesis studies.

Generally, in use, orbital shaker mechanism 110 will shake or stir the contents of flasks or vessels 116 as air is moved within air jacket 118, temperature control compartment 158, and workspace or chamber 108 in the manner shown in FIGS. 2 and 3. Specifically, fan 168 will move air across air conditioning unit 160 and heating unit 162 and be cooled or heated depending on which of these units is activated. The air will then move through air path 164, into air supply plenum 146, through HEPA filter 147 and perforated insert wall 124, and finally through workspace or chamber 108 in a single direction shown as left to right in FIGS. 2 and 3. Simultaneously, air will be forced from air supply plenum 146 into front and rear air plenums 138, 142 and into bottom plenum 154. Air will move across workspace or chamber 108 in the single direction shown in a substantially laminar fashion. Air is received into air return plenum 150 from workspace or chamber 108 through perforated end insert wall 126 and from front and rear air plenums 138, 142 (as shown best in FIG. 2). The air is then pulled back into temperature control compartment 158 from return plenum 150 through return air path 166 by fan 168.

It will be appreciated that air jacket insert 118 provides an economical and efficient manner of achieving a substantially isothermal wall condition for console shaker 100 by completely surrounding the periphery of workspace or chamber 108 and by further providing for an insulative air path below chamber 108. This provides an efficient, cost effective means of substantially isothermally insulating workspace or chamber 108 as well as providing a means for easily incorporating HEPA filtration of the air entering workspace or chamber 108 and substantially laminar air flow. By way of the air jacket feature of this invention as well as the control system to be described below, temperature within the workspace or chamber 108 may be controlled to within ±0.1° C. and temperature uniformity within workspace or chamber 108 is ±0.2° C.

The Control System

Figure 6:
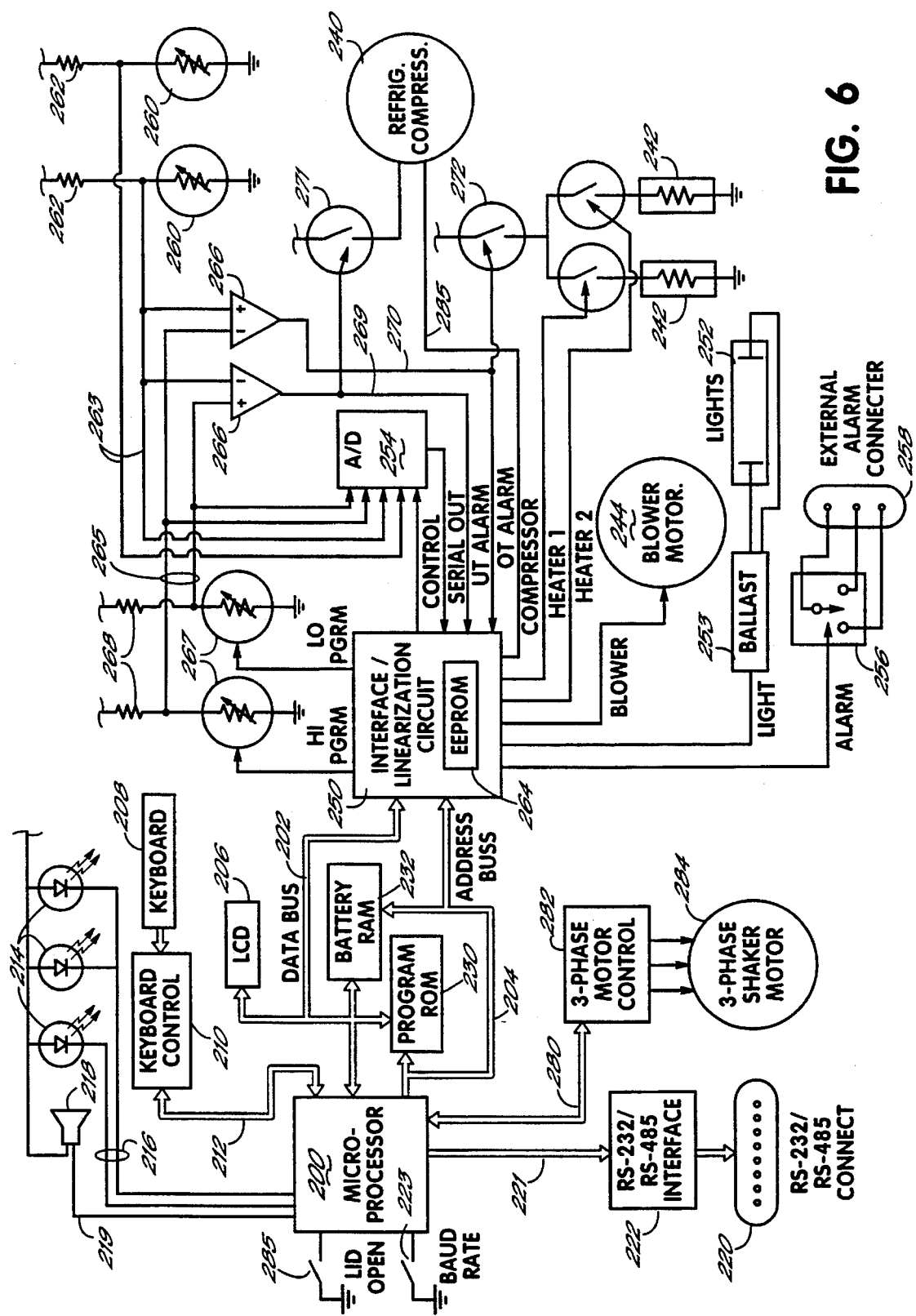
FIG. 6 is an electrical block diagram of the circuitry in the console shaker in accordance with principles of the present invention.

Referring to FIG. 6, the electrical circuitry inside console shaker 100 (FIG. 1) includes a number of discrete elements which can be illustrated in a block diagram. Console shaker 100 (FIG. 1) is controlled by a central microprocessor 200 having a number of input and output signal lines which will be discussed in further detail below. Microprocessor 200 is preferably designed to support a large number of input and output lines so as to facilitate control of circuitry inside of console shaker 100 (FIG. 1). One particularly suitable microprocessor is any member of the 68HC11 family of microprocessors sold by Motorola, Inc. of Schaumburg, Ill. Microprocessors of this family support, in addition to a data bus 202 and address bus 204, inputs for additional interrupt and signal lines such as those discussed below.

Microprocessor 200 displays data to an operator on a LCD screen 206 which is connected to microprocessor 200 by data bus 202. ASCII encoded data is written to LCD display 206 to provide information to the operator. The operator changes the settings of the microprocessor 200 and controls the operation of console shaker 100 (FIG. 1) through keystrokes at keyboard 208, which surrounds the LCD display 206 on the control panel. The manner in which these keystrokes are used in connection with the software in microprocessor 200 is discussed below. Keystrokes from keyboard 208 are read by a keyboard control circuit 210 which generates an interrupt signal for microprocessor 200 upon detection of a keystroke at keyboard 208. Lines 212 carry this interrupt and an indication of the key number to microprocessor 200.

The front panel of console shaker 100 also includes three LEDs 214 which are connected through lines 216 to microprocessor 200. In an alarm condition, microprocessor 200 causes LEDs 214 to flash to alert the operate of the alarm condition. This operation is discussed in further detail below.

Also included on the control panel of the shaker is a speaker 218. Microprocessor 200 can also indicate an alarm condition by causing speaker 218 to create warning tones via a signal on line 219.

Microprocessor 200 also produces output information at an RS-232/RS-485 connector 220 located on the rear panel of console shaker 100 (FIG. 1). To do so, microprocessor 200 produces output information on lines 221 which are received by a commercially available RS-232/RS-485 interface circuit 222 and there converted for output in RS-232/RS-485 format at connector 220. The nature of the data available through connector 220 is discussed in further detail below. The baud rate of information transmitted by microprocessor 200 through circuit 222 and connector 220 is determined by a jumper switch 223 connected to the microprocessor 200.

Microprocessor 200 performs operations in response to software found in a program read-only memory (ROM) 230. An exemplary program for program ROM 230 can be found in the microfiche appendix attached to this application. This program is written in the Forth-83 source language. Microprocessor 200 includes a Forth-83 compiler and interpreter for performing specific operations in response to Forth statements found in program ROM 230. A microprocessor including a Forth-83 compiler can be purchased from New Micros Incorporated, 1601 Chalk Hill Road, Dallas, Tex. 75212.

During operation of console shaker 100 (FIG. 1), microprocessor 200 stores and retrieves a number of operating settings as discussed in further detail below. These operating settings are stored in a random access memory (RAM) 232. RAM 232 is battery-backed ram, so that data stored in RAM 232 is not lost when power is removed from console shaker 100 (FIG. 1). Therefore, settings and programs entered by the operator will remain through a power shut down.

Microprocessor 200 performs temperature control functions by controlling a refrigerator compressor 240, heat generating resistors 242, and a blower motor 244 via an interface/linearization circuit 250. Microprocessor 200 uses interface/linearization circuit 250 to forward commands to compressor 240, heater resistors 242, and a blower motor 244 to turn these elements "on" and "off" to respectively cool, heat, or ventilate console shaker 100 (FIG. 1). Microprocessor 200 also controls a light source 252 (which may be one or more fluorescent lights powered by a power conversion ballast 253), via control signals relayed through interface/linearization circuit 250. In addition, microprocessor 200 uses interface/linearization circuit 250 to read temperature information produced by an analog temperature circuit and digitized A/D converter 254. Finally, interface/linearization circuit 250 controls an alarm relay 256 which forms an electrical connection between terminals of an external alarm connector 258. As noted below, in an alarm condition microprocessor 200 causes relay 256 to switch to an alarm position, creating an electrical connection which can be detected by circuitry connected through external alarm connector 258.

The temperature sensing circuit of console shaker 100 (FIG. 1) includes two thermistors 260 having a resistance which varies as a function of their temperature. These thermistors 260 are arranged in a voltage divider circuit with fixed resistances 262. As a result, the voltages on lines 263 are related to the temperature detected at thermistors 260. Lines 263 are connected to A/D converter 254, so that the analog voltages on lines 263 can be digitized and read by microprocessor 200 and used to control the operation of the compressor 240 and/or heaters 242. The software in program ROM 230, interacting with microprocessor 200, provides control of the temperature of the chamber in console shaker 100 (FIG. 1) in accordance with the operator set points and control parameters, To facilitate temperature measurement by microprocessor 200, interface/linearization circuit 250 includes an electrically erasable programmable read-only memory (EEPROM) 264. Memory 264 stores a table of calibration values, used with a look up table in program ROM 230, to associate voltage levels measured on lines 263 to the corresponding temperatures of thermistors 260. This calibration table is generated during calibration of console shaker 100 (FIG. 1) and is thereafter used in connection with a look up table stored in program ROM 230 to linearize and calibrate the behavior of thermistors 260 over the temperature ranges of interest. This calibration table is stored in an EEPROM within interface/linearization circuit 250, which is on a different printed circuit board than the microprocessor 200 and various other circuitry shown in FIG. 6. As a result, during calibration, interface/linearization circuit 250 and the remaining circuitry to which it connects can be calibrated by removing only the circuit board containing circuit 250, connecting this board to a calibration device which reads temperature data from circuit 250 and stores linearization information in EEPROM 264. Subsequently, when the board containing circuit 250 is installed into console shaker 100 (FIG. 1) with microprocessor 200, the previously stored calibration table in EEPROM 264 can be accessed by microprocessor 200 and used to calibrate readings obtained by thermistors 260.

It will be noted that there are two thermistors 260 for measuring the temperature in console shaker 100 (FIG. 1), and the voltages produced by these thermistors are independently supplied to A/D converter 254. One thermistor 260 serves as a main or primary temperature sensor which is used by microprocessor 200 to control the refrigerator compressor 240 and the heater resistors 242. The second thermistor 260 is used solely as a backup thermistor to determine whether the main or primary thermistor is functioning properly. As will be elaborated below, the temperature control software reads both thermistors 260 and, assuming the readings from the two thermistors are in close agreement, the temperature of console shaker 100 (FIG. 1) is controlled using the reading from the main thermistor 260.

In addition to the software temperature control provided by microprocessor 200, the shaker circuitry includes a separate and independent hardware temperature control system. This hardware temperature control system is an emergency backup system used to prevent damage if the software temperature control system fails. The heart of this hardware temperature control circuit is a pair of comparators 266 which compare the voltage produced on a line 263 by the secondary temperature sensor to two threshold voltages on lines 265. The threshold voltages are produced by voltage divider circuits including digitally programmable resistances 267 and fixed resistances 268. Lines 265, carrying these digitally programmed voltages, lead to a respective one of the comparators 266. The outputs of comparators 266 on lines 269 and 270 are digital signals indicating respectively that the temperature within console shaker 100 (FIG. 1) is below the acceptable range, or above the acceptable range. The output on line 269 is formed by comparing the voltage produced by a thermistor 260 to the voltage produced by a low temperature threshold programmable resistor 267 in response to a LO PGRM digital signal from interface/linearization circuit 250. If the voltage produced by the thermistor 260 is below the voltage produced by the programmable resistor 267, a high voltage will appear on line 269 indicating that the shaker voltage is below the acceptable threshold. In this condition, a relay 271 connected to line 269 will be opened, disconnecting power from the refrigerator compressor 240 and preventing further reduction of the temperature within console shaker 100 (FIG. 1). The signal on line 270 is produced by a comparator 266 by comparing voltages of the thermistor 260 to the voltage produced by a high temperature threshold programmable resistor 267 in response to digital programming signals on the line HI PGRM from the interface/linearization circuit 250. If the voltage from the thermistor 260 is greater than the threshold voltage produced by the programmable resistor 267, a high value will appear on line 270. In this condition, relay 272 will be opened preventing power from flowing to either of heaters 242, thus preventing any further over temperature in console shaker 100 (FIG. 1).

The digital signals indicating an under temperature alarm and an over temperature alarm on lines 269 and 270 also connect to interface/linearization circuit 250, and can be read via data bus 202 by microprocessor 200. Thus, during its normal software routine for temperature control, microprocessor 200 can read the hardware over-temperature and under-temperature alarm signals to determine whether a hardware alarm has been activated. These operations are discussed in further detail below.

In addition to the temperature control functions described above, microprocessor 200 includes a set of output lines 280 which lead to a three-phase motor control circuit 282. The three-phase motor control circuit provides three-phase voltage and current waveforms to a three-phase shaker motor 284 to generate a motor speed (RPM) requested by microprocessor 200 via signals on lines 280. Motor control circuit 282 also provides feedback on the current motor speed to microprocessor 200 via signals on lines 280. The operations of three-phase motor controller 282 are preferably performed by a programmed microcontroller such as a PIC17C42 microcontroller, available from Microchip Technology, Inc., Chandler, Ariz. The microfiche appendix attached hereto includes software written to control this microcontroller, in a source language which can be compiled by a compiler available from Microchip Technology at the above address.

Microprocessor 200 also includes a line connected to a lid open switch 285. This switch is coupled to lid 104 of console shaker 100 (FIG. 1), and indicates whether the lid 104 of console shaker 100 (FIG. 1) has been opened. If the lid is open, switch 285 produces a digital signal which can be detected by microprocessor 200.

Figure 7:
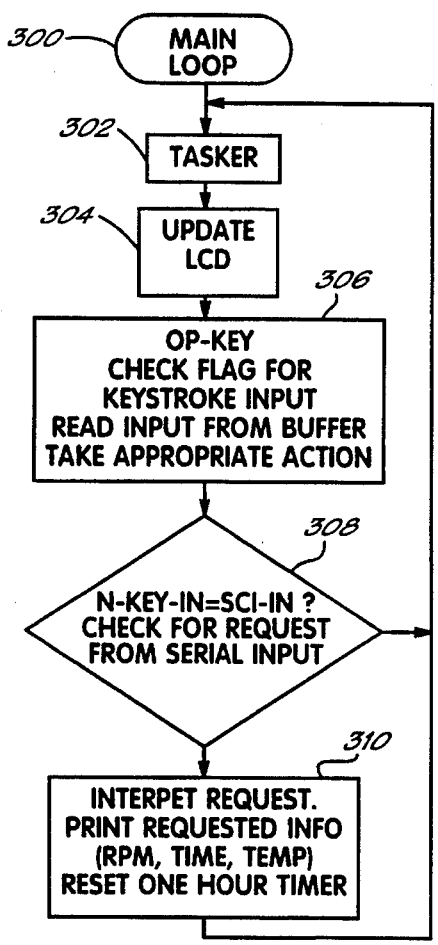
FIG. 7 is a flow chart of the main program loop performed by microprocessor 200 in the console shaker in response to software.
Figure 10C:
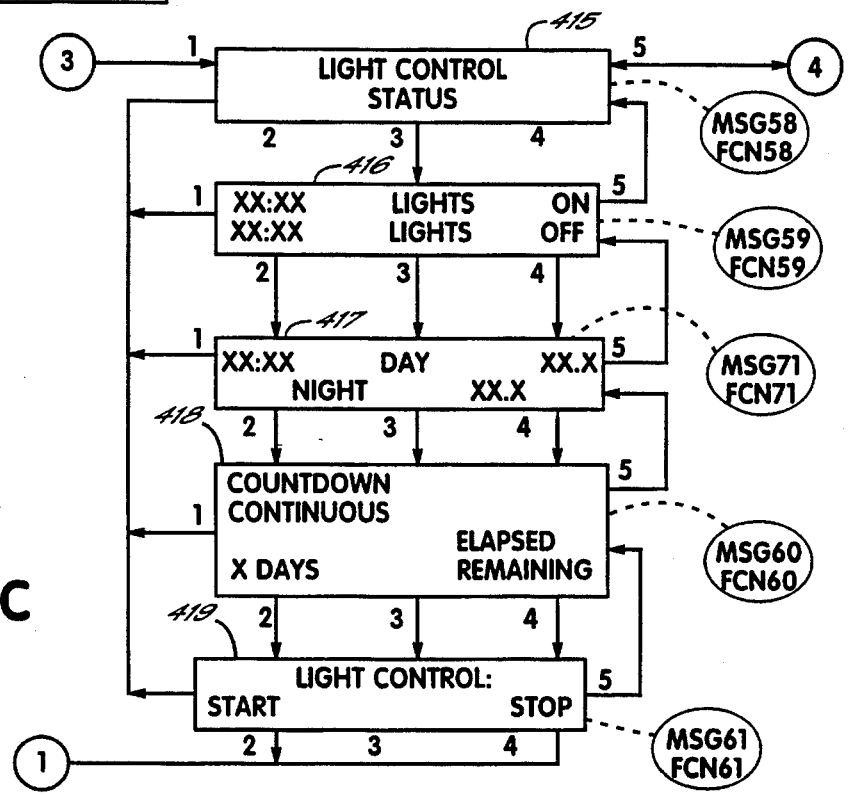

Referring to FIG. 7, the software in microprocessor 200 follows a main program loop 300 including a sequence of steps. At the beginning of this loop is a TASKER step 302 which invokes one of a sequence of tasks which are described in greater detail in FIG. 8. As is elaborated in further detail below, the operations performed by the TASKER step include all of the temperature control and various other functions discussed with reference to FIG. 6. The functions provided by TASKER step 302 are performed in a round-robin fashion as will be discussed in further detail below. For ease of reference, in the following discussion the tasker step of the main loop may be referred to as simply the "TASKER".

After completing the TASKER step, the main loop proceeds to step 304 which is a routine UPDATE_LCD. This routine produces a display corresponding the current state of the console shaker operation and places this display into the LCD 206. After this has been completed, the main program loop proceeds to step 306, ?OP-KEY. In this step, microprocessor 200 checks a internal flag to determine whether a keystroke has been received. If so, the keystroke is read from a keystroke buffer in RAM 232 and the appropriate action is taken in response to the keystroke. After this processing, the main program loop proceeds to step 308 in which the microprocessor determines whether a request has been received from the serial input via connector 220. If not, microprocessor 200 returns to the TASKER step 302. However, if a request has been received, microprocessor 200 proceeds to step 310 at which it interprets the received request, and prints (i.e., outputs via connector 220) the requested information, which typically includes the current shaker RPM, the elapsed time, and the current temperature. Finally, microprocessor 200 resets an internal one hour timer which is used, as discussed below, for automatic generation of information on connector 220. Following step 310, the main loop returns to the TASKER step 302.

Referring to FIG. 8, the TASKER performs one of a number of tasks in a round-robin fashion. Each time the main loop reaches the tasker step 302, one of the tasks identified in FIG. 8 is performed, and then the main loop continues to step 304. The next time the main loop reaches the tasker step 302, the next task identified in FIG. 8 is performed, and then the main loop continues to step 304. This process continues, performing each of the tasks identified in FIG. 8 in sequence in a round-robin fashion during iterations of the main loop of FIG. 7. Thus, while the tasks of FIG. 8 are being performed in sequence, the main loop regularly updates the LCD display and receives keystrokes in steps 304 and 306, thus minimizing the keyboard and display delay times perceived by the operator. To perform this task round-robin, the TASKER uses a task pointer which identifies which of the 34 tasks on the task list in FIG. 8 is next to be activated. Each time the main loop of FIG. 7 reaches the TASKER, the task identified by the task pointer is activated and then the task pointer is adjusted to identify the subsequent task in the task list of FIG. 8. As will be seen below, some tasks directly modify the task pointer and thereby cause the microprocessor 200 to skip a given number of tasks in the task list under certain conditions. However, under normal conditions, the tasks in the task list on FIG. 8 are performed directly in sequence in the order in which they appear in FIG. 8.

The first task in the task list on FIG. 8 is the SKIP-1S-TSK task. This task checks a flag indicating that a one second interval has expired. If this flag is set, SKIP_1S_TSK clears this flag and allows the TASKER to sequence to the immediate subsequent task, UPDATE-RUNTIME. However, if this flag is not set, SKIP_1S_TSK updates the task pointer to skip the subsequent four tasks, causing the TASKER to next invoke SKIP-5S-TSK task. Thus, SKIP_1S_TSK causes the four tasks that follow it to be executed exactly one time each second. The flag used by SKIP_1S_TSK to determine when a one second interval has expired is set by an interrupt routine which is discussed below in FIG. 9B.

When invoked, the UPDATE-RUNTIME task retrieves a variable from RAM 232 indicating the elapsed time that the shaker has been running, increments this time by one second, and stores the result in RAM 232.

The ALM-TIME-TSK task provides a run time alarm feature that can be programmed by the operator. As discussed in further detail below, the operator may set a time duration for which the shaker should operate. This time duration is stored in RAM 232 and is regularly decremented as the shaker is running. Accordingly, when ALM-TIME-TSK is initiated (once per second), it decrements the time alarm counters stored in RAM 232. Subsequent operations performed by the TASKER cause an audible and visual alarm to be activated when these alarm times reach zero.

The RTN-DISP-TSK task provides a time-out feature for the display functions discussed in the following Figs. If the operator has entered a display other than the main display but has failed to make any keystroke activity for five minutes, the RTN-DISP-TSK will cause the display to return to its main display screen. To achieve this goal, the RTN-DISP-TSK decrements a counter each time it is activated. As discussed below with reference to FIG. 9A, this counter is reset to a value of five minutes each time a keystroke is input by the operator. If no keystroke has been input for five minutes, the RTN-DISP-TSK will decrement this counter to zero. When this counter reaches zero, the RTN-DISP-TSK causes the display to return to the main display screen.

As discussed in further detail below, console shaker 100 (FIG. 1) provides an ambient light control function, permitting the operator to program periods of ambient light and periods without ambient light. These time periods are managed by the task LHT-TIME-TSK. Each time the LHT-TIME-TSK task is initiated, it updates the light timers, and determines whether a change state of light 252 is needed, if so, the task changes the state of the light 252.

The next task is the SKIP-5S-TSK task. This task checks a flag which indicates that a five second interval has expired. (This flag is also set by an interrupt routine discussed below with reference to FIG. 9B.) If the five second interval has expired, SKIP-5S-TSK clears the flag and permits TASKER to continue to the following task MTEMP?-TSK. However, if the flag has not been set, SKIP-5S-TSK updates the task pointer to skip the following 20 tasks and sequence directly to the ANNUNC-TSK task. Thus, the 20 tasks following SKIP-5S-TSK are executed once every five seconds, whereas the ANNUNC-TSK and the tasks which follow it are executed far more often in a round-robin fashion by TASKER.

The first task following SKIP-5S-TSK is MTEMP?-TSK. In this task, microprocessor 200 checks a flag indicative of whether a temperature controller is installed in console shaker 100 (FIG. 1). If there is no temperature controller, a flag indicating this causes MTEMP?-TSK to skip the following 13 tasks.

If there is a temperature controller, processing proceeds to the RD-MTEMP task. In this task, microprocessor 200 reads the temperature from the main temperature sensing thermistor 260. To do so, microprocessor 200 causes A/D 254 to convert the voltage on a line 263 from the thermistor 260 to a digital signal, and read the digital signal from the serial output line of A/D 254 through interface/linearization circuit 250.

After reading the main temperature sensor reading, microprocessor 200 executes the SHTDN-A/D task, which instructs the A/D converter 254 to set its serial out output to a high impedance level. Doing so eliminates potential bus conflicts in circuit 250.

Next, the LIN-MTEMP task is executed. In this task, microprocessor 200 uses the temperature sensor reading to index into the look-up and calibration tables stored in program ROM 230 and EEPROM 264. At the same time, an operator-programmable calibration offset (if any) is applied to the measured temperature value. (The programming of this value is discussed below with reference to display 444, FIG. 10G.) The result is a linearized, calibrated temperature sensor reading which is stored by microprocessor 200.

Thereafter, the CHK-M-T-SNSR task is executed by microprocessor 200. In this task, microprocessor 200 compares the temperature sensor reading to limits indicative of the maximum range within which the temperature should fall. If the temperature reading is outside of this range, this indicates an error in the temperature reading, and an alarm is initiated.

Next, microprocessor 200 executes the RD-OTEMP task. In this task, microprocessor 200 reads the analog voltage from the secondary temperature sensor 260, by causing A/D 254 to convert the analog voltage on line 263 from the secondary temperature sensor to produce a digital signal at its serial output line. This digital signal is retrieved by microprocessor 200 via circuit 250 and is stored in RAM 232.

After reading the over temperature sensor reading, microprocessor 200 again sets the serial out output of A/D 254 to a high impedance state using the task SHTDN-A/D.

Next, microprocessor 200 linearizes the over temperature sensor reading obtained from A/D 254 by executing the task LIN-OTEMP. In this process, microprocessor 200 uses the temperature sensor reading to index into the look-up table in program ROM 230 and the calibration table in EEPROM 264 to linearize and calibrate the temperature measurement value. The operator programmed calibration offset is also applied. The resulting value is stored in RAM 232.

Thereafter, microprocessor 200 executes the task CHK-O-T-SNSR, to compare the sensor reading to a range of possible values for the temperature sensor reading. If the temperature sensor reading is outside of this range, this is indicative of a flaw in the temperature sensing circuit and microprocessor 200 enables an alarm.

After thus reading the temperature within console shaker 100 (FIG. 1), microprocessor 200 executes the HEAT-TSK task. In this task, microprocessor 200 determines if the temperature controller is in use. If the temperature controller is not in use, microprocessor 200 skips the following 4 tasks which relate to the operation of the compressor 240 and heaters 242.

Assuming the temperature controller is enabled, microprocessor 200 executes the MTEMP-PID-TSK. In this task, microprocessor 200 uses proportional integral-derivative control to determine whether to activate the refrigerator compressor 240 or the heater resistors 242, or neither, to control the temperature of the shaker chamber 108 (FIGS. 2–4) to the desired set point. If the compressor 240 is to be activated, microprocessor 200 causes interface circuit 250 to produce a signal on line 285, causing compressor 240 to turn on. If the heaters 242 are to enabled, microprocessor 200 sets a flag in RAM 232. An interrupt discussed below with reference to FIG. 9C then causes the heater resistors to pulse "on" and "off".

After thus controlling the heater and/or compressor, microprocessor 200 executes the CHK-TEMP-HI-ALM and CHK-TEMP-LO-ALM tasks. In each of these tasks, the temperature reading obtained from the main temperature sensing thermistor 260 is compared to the set point. If the temperature reading is greater than the set point plus an operator programmable tracking limit, the CHK-TEMP-HI-ALM task will enable an over temperature alarm. Alternatively, if the temperature from the main temperature sensing thermistor is less than the set point temperature minus the operator programmable tracking limit, the CHK-TEMP-LO-ALM task will enable an alarm.

After checking for alarm conditions, microprocessor 200 executes the TEMP-AVG-TSK. In this task, microprocessor 200 averages the recent main temperature sensing thermistor readings, and stores the average reading for use as a display on LCD 206. By averaging recent temperatures readings in this way, the display on LCD 206 is made more stable.

Following the preceding tasks, which relate to temperature control, microprocessor 200 performs steps to control the speed of the shaker motor 284. First, microprocessor 200 executes the UPDATE-RPM task. In this task, microprocessor 200 sends the current RPM set point to motor controller 282, and requests a reading from motor controller 282 of the current RPM of motor 284. An operator calibration offset, if any, is then applied to the RPM reading from motor controller 282, and the resulting RPM reading is stored in memory. (The manner of programming this operator calibration offset is discussed below with reference to display 453, FIG. 10H.)

Thereafter, microprocessor 200 performs the CHK-RPM-HI-ALM and CHK-RPM-LO-ALM tasks, in which microprocessor 200 compares the current RPM reading to the operator defined set point, plus or minus the tracking limit. If the current RPM is in excess of the set point plus the tracking limit, CHK-RPM-HI-ALM enables an alarm. Alternatively, if the current RPM reading is less than the operator defined set point minus the tracking limit, CHK-RPM-LO-ALM enables an alarm.

Subsequent to the steps described above, microprocessor 200 produces alarm feedback to the operator through the ALM-DISP-TSK. In this task, microprocessor 200 determines whether an alarm is active, and if so, microprocessor 200 inserts a message indicating the alarm type into a queue of messages to be displayed by the UPDATE_LCD routine 304 (FIG. 7). As a result, a text message will appear on LCD display 206 indicating the kind of alarm which has been enabled.

Microprocessor 200 then executes the PRINT-TSK task. In this task, microprocessor 200 determines whether an internal one hour timer has expired. If this timer has expired, the current status of console shaker 100 (FIG. 1), including the RPM reading, temperature reading, and active time reading, is transmitted through RS-232/RS-485 interface 222 to connector 220. After thus printing this data, the one hour timer is reset.

The software in program ROM 230 also includes a diagnostic task PRINTI-TSK. This task is enabled only when the software in program ROM 230 has been written to enable diagnostics. This diagnostic task can be used to trouble shoot console shaker 100 (FIG. 1) by causing microprocessor 200 to print various information stored in RAM 232 on command from RS-232/RS-485 connector 220. Under normal operation, PRINTI-TSK is disabled, and microprocessor 200 skips over this task.

The next task executed by microprocessor 200 is ANNUNC-TSK. In this task, microprocessor 200 determines whether any alarm conditions have been activated. If there are any alarm conditions, microprocessor 200 sets a flag to cause the speaker to produce an alarm tone. An interrupt routine discussed below in reference to FIG. 9D causes this alarm tone to be produced by speaker 218 when the appropriate flag is set.

Thereafter microprocessor 200 executes the REM-ALMTSK task. In this task, microprocessor 200 determines if there are any active alarm conditions that should be reported to the external alarm connector 258. If so, microprocessor 200 directs interface circuit 250 to activate external alarm relay 256. Doing so will cause any external circuitry connected to connector 258 to generate an alarm signal.

Microprocessor 200 then executes the CHK-RESET-MSG task. In this task, microprocessor 200 determines if any alarm messages have been inserted into the display queue by the ALM-DISP-TSK task. If so, microprocessor 200 adds an additional reset message into the queue for display by UPDATE_LCD. This reset message indicates to the operator how to reset the active alarm by pressing one of the keys on the keyboard 208. This reset message will be displayed in sequence, along with the alarm text messages, by UPDATE_LCD. If, however, microprocessor 200 determines that there are no active alarms, and therefore no alarm messages in the queue for UPDATE_LCD, microprocessor 200 will remove this reset message from the queue so that the reset message will no longer be displayed.

Thereafter, microprocessor 200 checks the hardware under- and over-temperature alarm signals on lines 269 and 270, during the CHK-OT-ALM and CHK-UT-ALM tasks. Each task checks a respective digital signal on one of lines 269 and 270. If an over-temperature alarm signal on line 270 or an under-temperature alarm signal on line 269 is detected during either of these tasks, microprocessor 200 enables the corresponding software alarm. At the same time, the alarm signal on line 270 or 269 also disables either the heater or compressor, respectively.

Thereafter, microprocessor 200 executes the LID-SWTCH-TSK task. In this task, microprocessor 200 determines whether the lid switch 285 indicates that the lid 104 of console shaker 100 (FIG. 1) has been opened. If the lid has been opened, microprocessor 200 halts operation of motor 284 and of blower 244.

Finally, in the last task in the task list, VIS-ALM-TSK, microprocessor 200 determines if there are any alarm conditions active. If there is an alarm condition active, microprocessor 200 sets a flag to cause the LEDs 214 to flash and provide a visual alarm to the operator. An interrupt routine discussed below in connection with FIG. 9E responds to the setting of this flag by causing LEDs 214 to flash.

Referring to FIGS. 9A through 9E, the various timed interrupts discussed above cause activities to occur in response to flags set during tasks in the task list of FIG. 8.

Figure 9A:
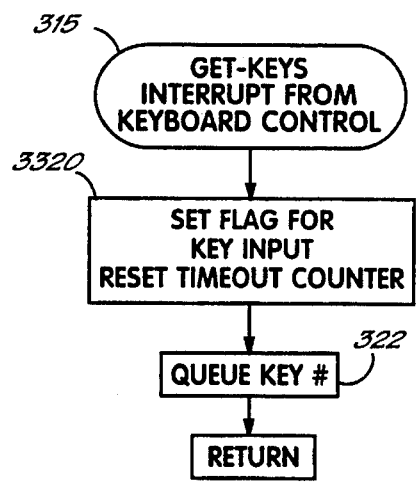
FIGS. 9A, 9B, 9C, 9D and 9E are flow charts of the interrupt routines performed by microprocessor 200 in response to software; and, FIGS. 10A, 10B, 10C, 10D-1, 10D-2, 10E, 10F, 10G, 10H AND 10I are flow charts illustrating the displays and key functions generated and performed by microprocessor 200 in response to software, permitting the operator to control and configure the console shaker in accordance with principles of the present invention.

Specifically, referring to FIG. 9A, interrupt GET-KEYS is activated by keyboard control circuit 210 via lines 212 whenever a key stroke is input to the keyboard and detected by keyboard control circuit 210. In this interrupt, microprocessor 200 sets a flag indicating that a key input has been received and resets the time-out counter used by the RTN-DISP-TSK task. Thereafter, microprocessor 200 reads the key number from keyboard control circuit 210 via lines 212, and stores the key number received into a queue of incoming keystrokes in RAM 232. Keystrokes are read from this queue by the ?OP-KEY operation 306 in the main loop of FIG. 7.

Figure 9B:
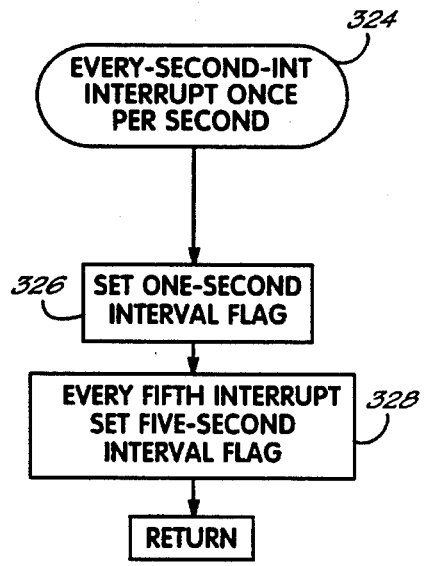
Figure 9C:
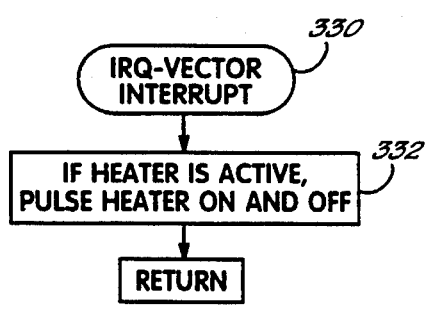
Figure 9D:
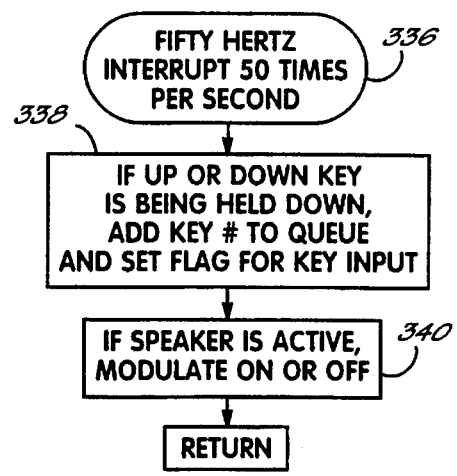
Figure 9E:
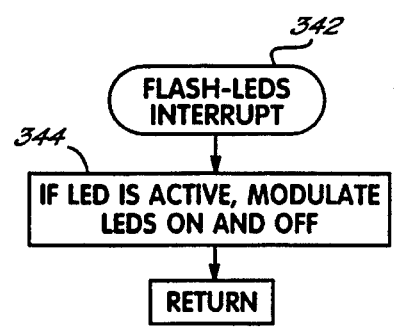

Referring to FIG. 9B, microprocessor 200 causes an interrupt EVERY-SECOND-INT 324 to be activated once each second. When this interrupt is activated, step 326 sets the one second interval flag, which is used by the SKIP_1S_TSK as discussed above. In addition, every fifth time that EVERY-SECOND-INT is activated, the interrupt sets 328 the five second interval flag, which is used by the SKIP-5S-TSK task as discussed above.

A third interrupt routine, IRQ-VECTOR 330, is also activated on a timed basis by microprocessor 200. When this interrupt is activated, it determines 332 whether the flag set by the MTEMP-PID-TSK task indicates that the heater should be active. If the heater should be active, this interrupt pulses the heater resistors 242 "on" and "off" between successive interrupts.

An additional interrupt, FIFTY-HZ 336, is activated by microprocessor 200 50 times each second. In this interrupt, microprocessor 200 determines whether the operator is holding down a key on the keyboard 208. If a key is being held down, the interrupt adds the key number for the key to the key queue and sets the flag in RAM 232 indicating there has been key input. This action causes an additional key stroke to be added to the key queue. Thus, if, for example, the operator presses and holds a key for incrementing or decrementing a value (see FIGS. 10A et seq. below), the FIFTY-HZ interrupt will cause repetition of the keystroke corresponding to the key that is being held down, so that the value is rapidly incremented or decremented without requiring multiple keystrokes by the operator. The FIFTY-HZ interrupt also determines 340 whether the speaker 218 is to be activated, from the flag set by the ANNUNC-TSK task discussed above. If so, the FIFTY-HZ interrupt modulates the digital signal on line 219 leading to speaker 218 "on" and "off" once every 25 interrupts. As a result, a 2 Hz signal is applied to speaker 218, providing power to speaker 218 and producing an alarm tone.

A final interrupt routine FLASH-LEDS 342 is activated on a regular timed basis by microprocessor 200 to produce a visual alarm from LEDs 214. In this interrupt, microprocessor 200 determines 344 whether the LEDs should be active by checking the flag which is set by the VIS-ALM-TSK task. If the LEDs should be active, microprocessor 200 alternately enables and disables the signals on lines 216 leading to the three LEDs 214, thereby causing an alternate flashing of LEDs 214 to produce a visual alarm.

Software provided in the attached appendix includes a plurality of message subroutines entitled MSG# (where # is a number), and a number of function tables entitled F#-TABLE (where # is a number). These message subroutines and function tables define a state machine which produces, in each state, a display on LCD screen 206 as defined by the MSG# message subroutine for that state. Each state also associates a set of actions with each key on the keyboard, which are defined by the F#-TABLE function tables. The operator controls console shaker 100 (FIG. 1) by depressing keys on keyboard 208, which keystrokes are processed by the ?OP-KEY step 306 (FIG. 7) in response to the functions defined by the F#-TABLE function table for the current state, causing microprocessor 200 to update variables and/or transfer the state machine into a new state.

Figure 5:
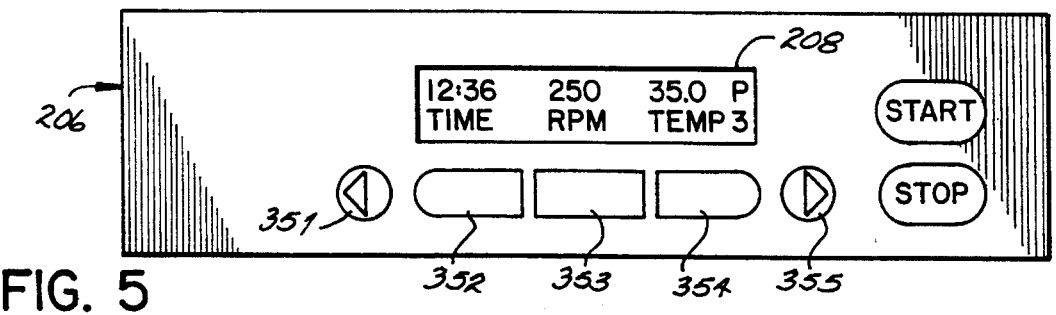
FIG. 5 is an enlarged front elevational view showing the display and keypad of the console shaker illustrated in FIG. 1.

As can be seen in FIG. 5, the keyboard includes a key 351 having a left movement arrow thereon and key 355 having a right movement arrow thereon. Between these keys are keys 352, 353 and 354 which are positioned directly below the LCD display 206 on the face of lid 104 of console shaker 100 (FIG. 1). The keys 351–355 are used by the operator to move from one display state to another, and to change various operational parameters as described in detail below. In each display state the keys 351–355 have differing functions depending upon the display state.

Referring to FIGS. 10A to 10I, the purpose of the states defined by the MSG# display subroutines and F#-TABLE function tables can be effectively understood by charting each display produced by a MSG# subroutine, and identifying the key functions for that display screen, and the transitions from one display screen to another.

Figure 10A:
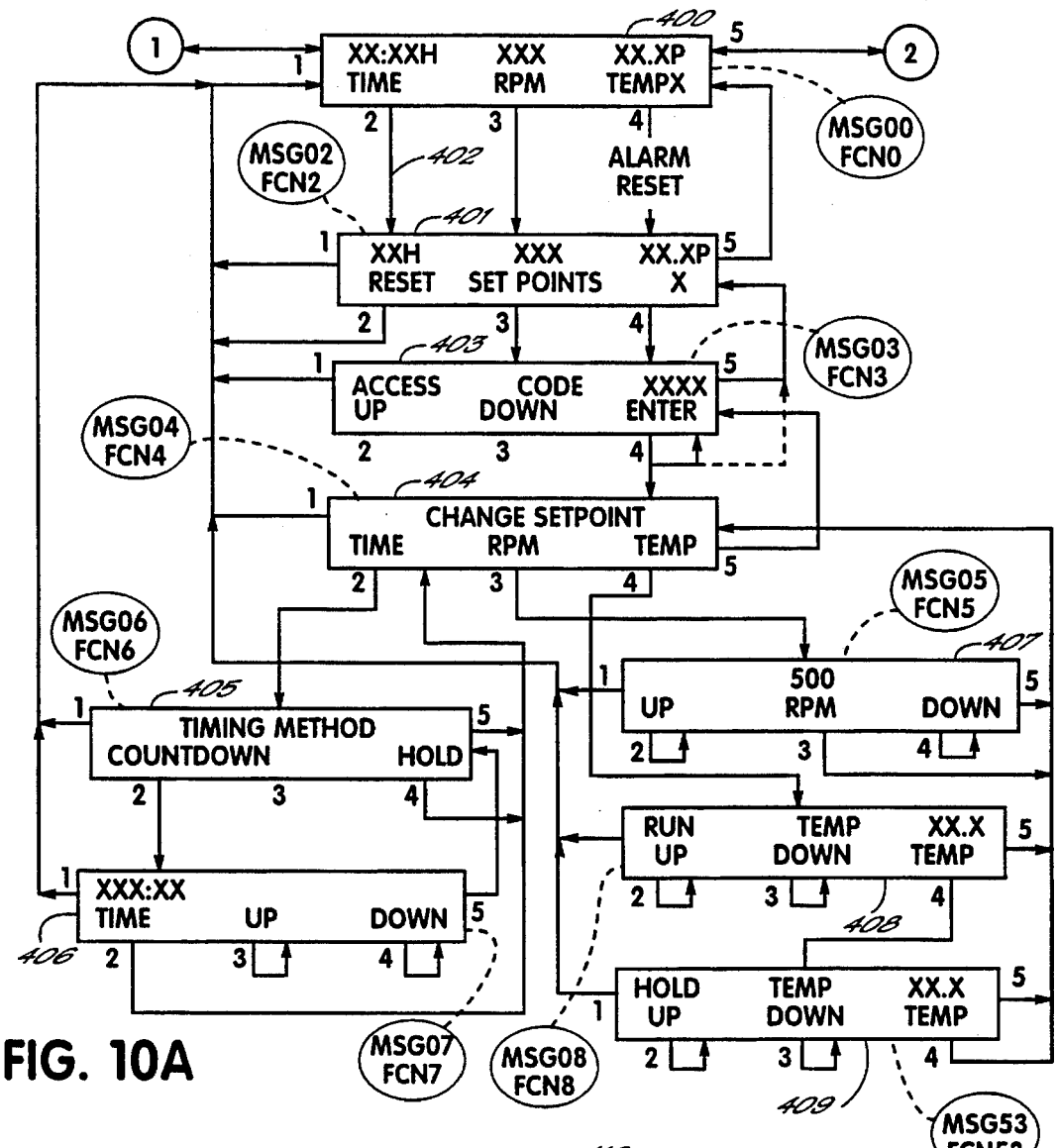
Figure 10B:
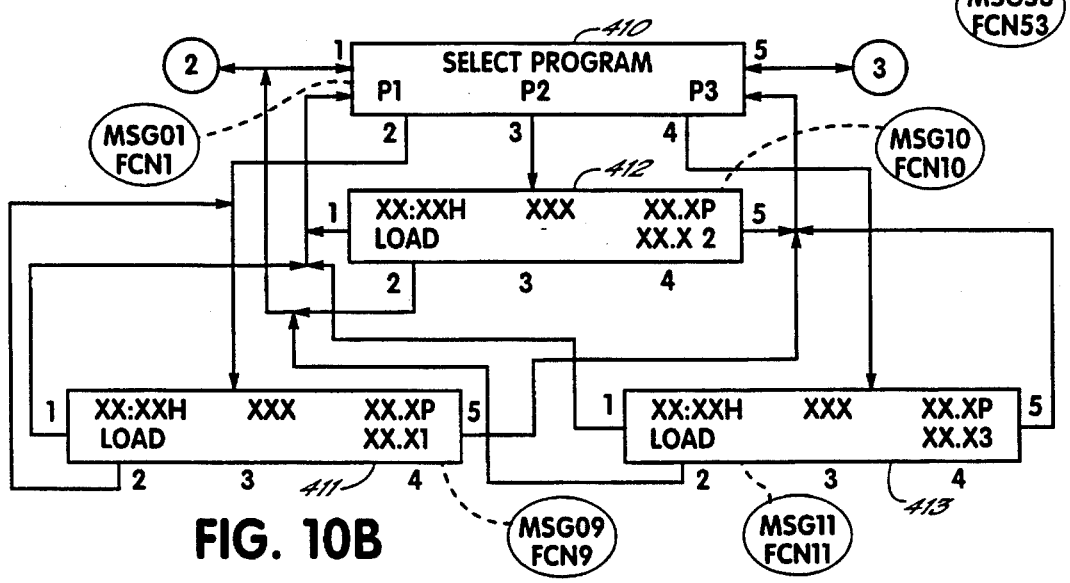
Figures 1, 10D:
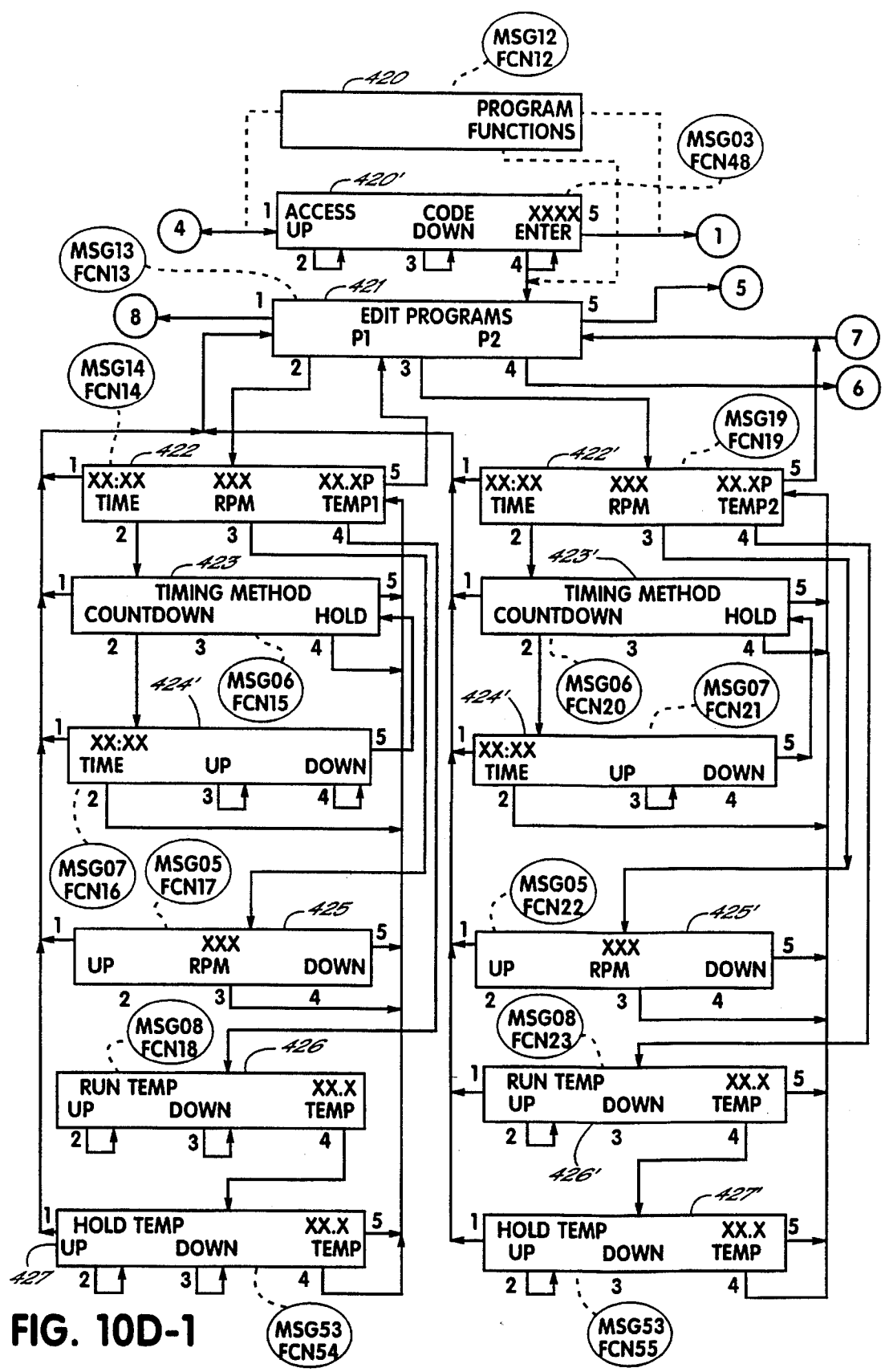
Figures 2, 10D:
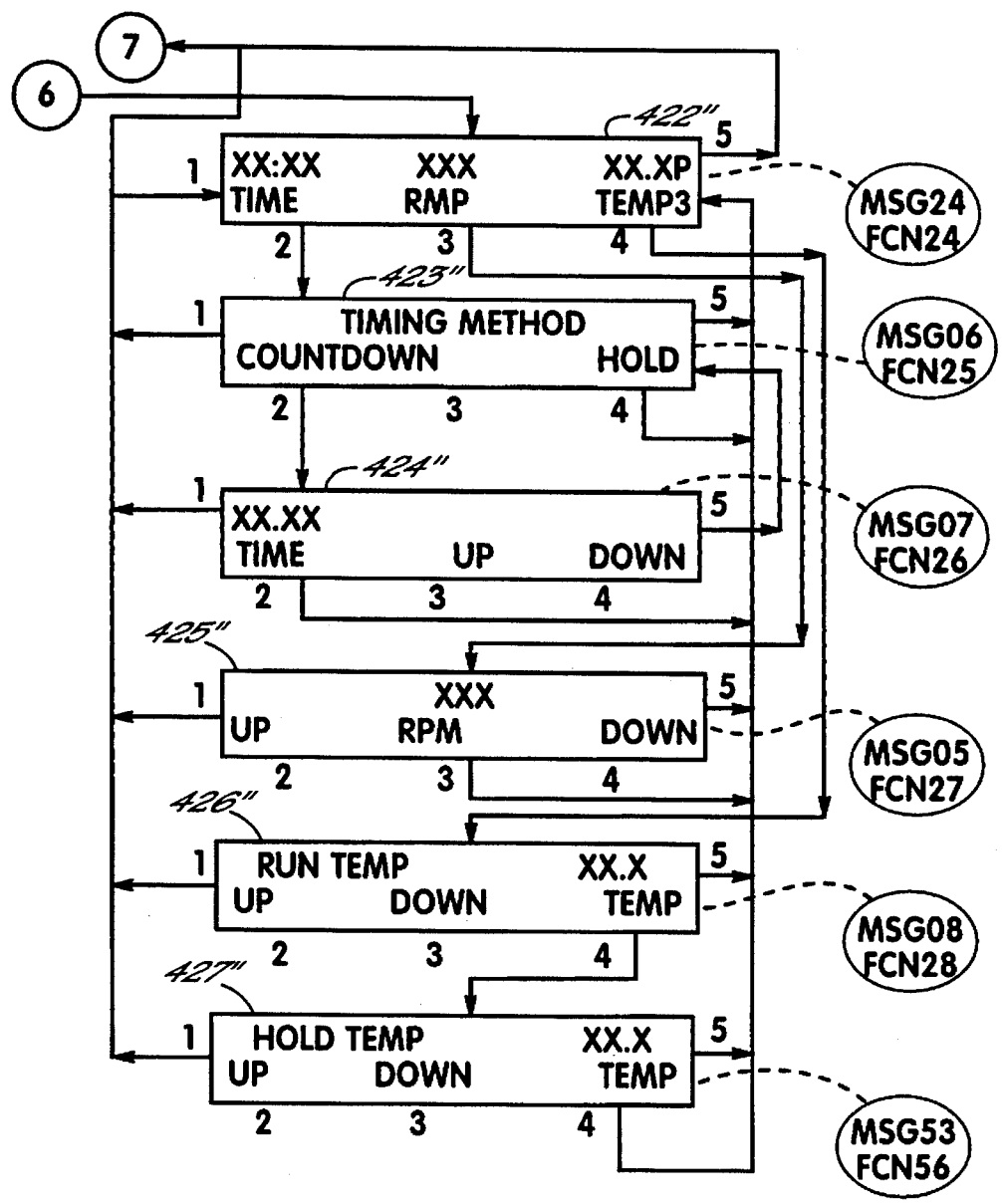

FIG. 10A shows the main operating display 400 which is produced by LCD 206 during normal operation corresponds to message subroutine MSG00 and function table F0-TABLE. In this main operating display 400, the first line of LCD 206 displays the current accumulated runtime, the current RPM reading from the shaker motor, and the current temperature reading from the temperature controller. The lower line of the LCD 206 displays the words TIME, RPM, and TEMP. Thus, the main operating window indicates the current run time, RPM and temperature of chamber 108 (FIGS. 2–4). The run time indicates either the duration of time that the shaker has been operating, or the time remaining until automatic shut-down of the console shaker, depending on the timing method selected by the operator.

As indicated in FIG. 10A, the operator may move from this main operating display to a number of related displays to adjust the operating parameters of console shaker 100 (FIG. 1). These changes are accomplished by pressing one of the five keyboard keys 351–355. For the purposes of brevity, in FIG. 10A and the following Figs., the keystroke associated with a transition from one display to the next is indicated by a key number 1, 2, 3, 4, 5, corresponding respectively to keys 351, 352, 353, 354 and 355 on keyboard 208. Thus, by depressing key 352 on keyboard 208 when microprocessor 200 is displaying display 400 of FIG. 10A, the operator can cause microprocessor 200 to transition to display 401 of FIG. 10A; this transition is indicated by an arrow 402 extending from display 400 to display 401, and the numeral 2 positioned adjacent to arrow 402 at its intersection with the exterior of display 400. Similarly, the operator can transition to display 401 by pressing keys 353 or 354 on keyboard 208.

As can be seen by comparing relative positions of the words TIME, RPM and TEMP and the positions of buttons 352, 353 and 354, as illustrated in FIG. 5, it can be seen that button 352 appears adjacent to the word "TIME" in the display, and similarly the words "RPM" and "TEMP" appear in the display adjacent to buttons 353 and 354. Accordingly, in the main operating screen and in various other displays that are produced by microprocessor 200, the significance of the three buttons can be determined by comparing the positions of the three buttons 352–354 to the text appearing directly above those buttons in LCD 206.

Thus, when the operator wishes to change the current time, RPM, or temperature set points, the operator presses one of buttons 352, 353 or 354 to move the display to display 401. Display 401 indicates in the upper line of LCD 206 the current time, RPM and temperature set points, and in the lower line of LCD 206 includes the text "(RESET) SETPOINTS". Thus, this display indicates to the operator that by pressing key 352, the setpoints may be reset to factory defaults, and by pressing either of keys 353 or 354, the current setpoints may be changed.

If the operator presses key 353 or 354 while in display 401, the operator will begin the process for adjusting the setpoints of console shaker 100 (FIG. 1). In this situation, console shaker 100 (FIG. 1) includes a safety feature which prevents unauthorized access of the preprogrammed setpoints. To prevent such unauthorized access, microprocessor 200 stores a four digit access code which must be supplied by the operator before setpoints can be modified. This access code will be required before any modifications are made to preprogrammed setpoints or other operating parameters. However, if the access code is set to the four digit number 0000, then microprocessor 200 will disable this access protection feature and will not require entry of the access code before changing preprogrammed setpoints or operating parameters.

Thus, if the operator presses either key 353 or 354 when in display 401, microprocessor 200 will determine whether the access code is 0000, and if not, microprocessor 200 will transition to display 403 in which the operator must supply the correct access code to continue further. If, however, the access code is 0000, the operator may proceed directly to display 404 at which the setpoints may be changed. To enter an access code at display 403, the operator may press either of keys 352 or 353 to respectively increase or decrease the value of a digit in the access code. When the correct digit value has been reached, the operator presses key 354 (associated with the text "ENTER") to move to the next digit in the access code. When all four digits in the access code have been entered in this way, microprocessor 200 will transition to display 404 if the access code has been entered correctly; otherwise, microprocessor 200 will return to display 401.

Once the operator has arrived at screen 404, the operator may change the current time, RPM, or temperature setpoints, by pressing one of keys 352–354, each of which is associated with one of "TIME", "RPM" and "TEMP" in the lower line of LCD 206. If the operator presses key 352 associated with "TIME", microprocessor 200 will proceed to display 405 in which the operator may change the timing method used by the microprocessor 200. At this point, if the operator presses key 354, associated with the word "hold", microprocessor 200 will change its timing operations into a mode in which the accumulated operating time is displayed at display 400 and console shaker 100 (FIG. 1) runs continuously until it is stopped, and return to display 404. Alternatively, if the operator presses key 352, associated with the word "countdown", microprocessor 200 will place the console shaker in an operating mode in which the console shaker will operate only until a predetermined specific operating time has expired. In this case, microprocessor 200 transitions to display 406 in which the operator is asked to identify the desired countdown time. In display 406, the operator may press key 353 or key 354, respectively associated with the words "up" and "down" to increase or decrease the countdown time identified in the first line of LCD 206. When the desired countdown time is achieved, the operator may press key 352, associated with the word "time", to store the new countdown time value and return to display 404.

To adjust the current RPM set point, the operator may depress key 353 to cause microprocessor 200 to transition to display 407. Once in display 407, the operator may increase or decrease the current RPM setting (shown in the center of the first line in LCD 206) pressing either key 352 (associated with the word "up") or key 354 (associated with the word "down"). When the desired new RPM set point has been reached, the operator may store this new setting by pressing key 353 ("RPM").

To change the current temperature set points, when the operator is in display 404, the operator may press key 354 to move to displays 408 and 409. Display 408 shows the current "run" temperature set point. This is the temperature that the temperature controller will maintain while the shaker motor is running. In this display, the operator may press keys 352 ("up") and 353 ("down") to change the current run temperature set point. Then, by pressing key 354 ("Temp"), or key 355, the operator may store the new run temperature set point and move ot display 409. Display 409 shows the current "hold" temperature set point. This is the temperature that the temperature controller will maintain after the shaker motor has turned off as a result of expiration of a timer. In this display, the operator may press keys 352 ("up") and 353 ("down") to change the current hold temperature set point.

It will be noted in FIG. 10A, that each display 400, 401, 403, 404, 405, 406, 407, 408 is associated with a message subroutine MSG# and a function table FCN#. As noted above, microprocessor 200 uses a message subroutine to produce each of the respective displays and uses a function table unique to each display to transition from that display to other displays and/or to perform operations on the display. In the following Figs., each display is associated with the respective message subroutine and function table which produce the display and enable the functions illustrated in the Figs.

In addition to selecting individual set points for operation of console shaker 100 (FIG. 1), the operator may retrieve preset programs of set points stored in RAM 232 by microprocessor 200. To select one of these preset programs, the operator when in display 400, presses key 355 on keyboard 208, transitioning to display 410 illustrated in FIG. 10B.

In display 410, the first line of LCD 206 indicates "select program", indicating that the operator may use this display to select one of three predefined programs of operating points for console shaker 100 (FIG. 1). The operator may select the first predefined program by pressing key 352 ("P1"), may select the second predefined program by pressing key 353 ("P2"), and may select the third predefined program by pressing key 354 ("P3"). When a respective one of keys 352, 353, and 354 is depressed, microprocessor 200 moves to a respective one of displays 411, 412 and 413. In each of these displays, the first line of LCD 206 indicates the time, RPM, and run temperature settings of the predefined program. The bottom line of the LCD 206 includes the word "load" associated with key 352, and also indicates the hold temperature setting of the predefined program. Thus, by depressing key 352 in any of displays 411, 412 or 413, the operator may select the predefined set points indicated in the display. Microprocessor 200 will store these predefined set points for use in controlling the console shaker, and then return to display 400 (FIG. 10A).

In addition to, or instead of using predefined set points for time and temperature, the operator may program console shaker 100 (FIG. 1) to perform day and night simulation using light(s) 252 and temperature control settings. This functionality is achieved by pressing key 355 in display 410, which causes microprocessor 200 to transition to display 415 shown in FIG. 10C. Display 415 and the following displays are used to cause microprocessor 200 to perform a preprogrammed day and night simulation in accordance with preprogrammed parameters. Specifically, by pressing key 353 ("status"), the operator may move to display 416 which indicates the time which lights 252 will be illuminated to simulate daytime, and the time which lights 252 will be extinguished to simulate nighttime, both times being identified relative to the start of a 24-hour period. Pressing any of keys 352, 353, or 354 moves microprocessor 200 to display 417 which indicates the temperatures to be produced by the console shaker to simulate day and night. Pressing any of keys 352–354, moves microprocessor 200 to display 418 which indicates whether day/night simulation is to be generated continuously by the console shaker as long as the console shaker is turned on, or alternatively, is to be produced for a specified number of days, and also displays the number of days simulated thus far and/or alternatively the number of days remaining to be simulated. Finally, depressing any of keys 352–354, transitions microprocessor 200 to display 419 which indicates whether the day/night simulation is active. If day/night simulation is desired, the operator may press key 352 ("start") to start day/night simulation. Alternatively, if the operator wishes to disable day/night simulation, the operator may press key 354 ("stop").

The foregoing describes the manner in which preprogrammed parameters and functions can be selected by the operator for use of console shaker 100 (FIG. 1). The operator may also change these preprogrammed functions and parameters by use of additional displays described below. Specifically, by pressing key 355 at display 415 or by pressing key 351 at the main display 400, the operator may arrive at display 420 or 420', which lead to displays used to program the console shaker. Here, as discussed above, if the four digit access code is not 0000, the operator will first be presented with display 420' which requires the operator to enter the access code in the manner discussed above with references to display 403. If, however, the access code is the four digit number 0000, the operator will be presented with display 420 including the message "Program functions". Once the access code has been entered (if needed) the operator may press key 354 to move from display 420 or 420' to display 421 begin setting the operating parameters and predefined programs for console shaker 100 (FIG. 1).

Display 421 is used to define the time, RPM and temperature settings for each of the three predefined programs which can be accessed through display 410 (FIG. 10B) discussed above. Specifically, the operator may press one of buttons 352, 353 or 354 to modify one of the programs P1, P2 or P3, respectively. In each case, the operator will be presented with a display 422 (or 422' or 422") indicating the time, RPM and temperature settings for the respective program P1, P2 or P3. Then the operator may press one of keys 352, 353 or 354 ("time", "RPM", or "temperature", respectively) to modify one of the time, RPM or temperature settings for the selected program P1, P2 or P3. If key 352 is depressed, microprocessor 200 transitions to display 423, 423' or 423" in which microprocessor 200 indicates whether the selected program uses countdown timing, (i.e. operating the console shaker for a predetermined period of time) or hold timing (i.e. operating the console shaker for an indefinite period of time). If the operator desires hold timing, the operator depresses key 354; if the operator desires countdown timing, the operator depresses 352, causing microprocessor 200 to proceed to display 424, 424' or 424". In these displays, the operator may indicate the desired countdown time in the same manner as discussed above with reference to display 406 (FIG. 10A).

If the operator wishes to change the RPM setting for the selected program P1, P2 or P3, the operator depresses key 353 ("RPM") in display 422, 422' or 422". Doing so causes microprocessor 200 to proceed to display to 425, 425' or 425", respectively. In this display, the operator may set the preprogrammed RPM level in the same manner as discussed above with reference to display 407 (FIG. 10A).

Finally, if the operator wishes to adjust the temperature set points for one of the programs P1, P2 or P3, the operator may depress key 354 while in display 422, 422' or 422", respectively. Doing so causes microprocessor 200 to transition to displays 426, 426' or 426", respectively. In these displays, the operator may adjust the run temperature set point for the respective program in the same manner as discussed above with reference to display 408 (FIG. 10A). Thereafter, the operator transitions to displays 427, 427' or 427", respectively, where the operator may adjust the hold temperature set point for the respective manner as discussed above with reference to display 409 (FIG. 10A).

Figure 10E:
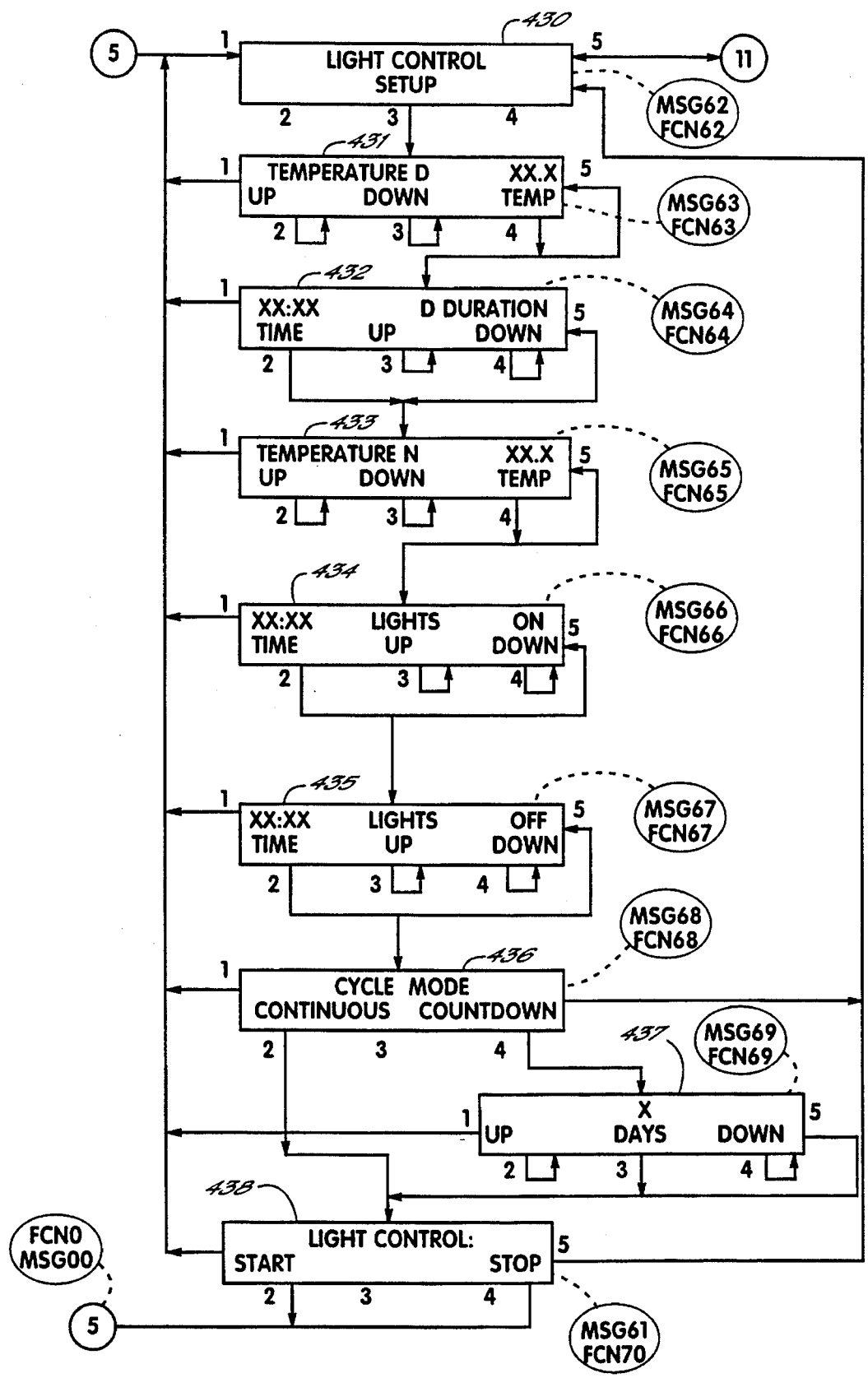

The operator may also change the light control programming in a similar manner, by moving to display 430 (FIG. 10E). To move to display 430, the operator may depress key 355 while in display 421, causing microprocessor 200 to transition to display 430. Once in display 430, the operator may depress key 353 ("set up"), to move to display 431. Display 431 indicates the daytime temperature for the light control and permits the operator to adjust this temperature up using key 352 or down using key 353. Once the desired daytime temperature is set, the operator depresses key 354 to move to display 432. Display 432 indicates the duration of daytime simulated operation. To change the simulated daytime duration, the operator depresses keys 353 ("up") or key 354 ("down"). When the desired daytime duration is set, the operator depresses key 352 to transition to display 433. (The nighttime simulated duration is equal to the daytime simulated duration subtracted from 24 hours.) Display 433 indicates the simulated nighttime temperature in a similar manner to display 431. This nighttime temperature may be adjusted with keys 352 and 353 in the same manner as discussed above with reference to display 431. Key 354 causes microprocessor 200 to transition to display 434 which indicates the number of hours and minutes after the light control is turned on at which lights 252 are to be turned on to simulate daytime. This time may be adjusted by pressing keys 353 ("up") or 354 ("down"). When the desired lights on time has been set, the operator presses key 352 to transition to display 435. Display 435 indicates the number of hours and minutes after the light control is turned on when the lights should be turned off to simulate nighttime. This time can be adjusted in a similar manner as discussed above by pressing keys 353 ("up") and 354 ("down"). When the desired off time has been identified, the operator presses key 352 to transition to display 436. Display 436 indicates whether the day/nighttime simulation should be continuous or should be performed for a number of simulated days. The operator can select continuous operation by pressing key 352 in which case microprocessor 200 will directly transition to display 438. The operator may also select operation for a specified number of days by pressing key 354 ("countdown"), causing microprocessor 200 to transition to display 437. Display 437 indicates the number of simulated days to be generated by the console shaker. The operator may adjust this number of simulated days by pressing key 352 ("up") or key 354 ("down"). When the desired number of days have been selected, the operator presses key 353 to proceed to display 438. At display 438, the operator may indicate whether the light control is to be enabled of disabled by pressing key 352 ("start") or key 354 ("stop") in a manner similar to that discussed above with reference to display 419.

Figure 10F:
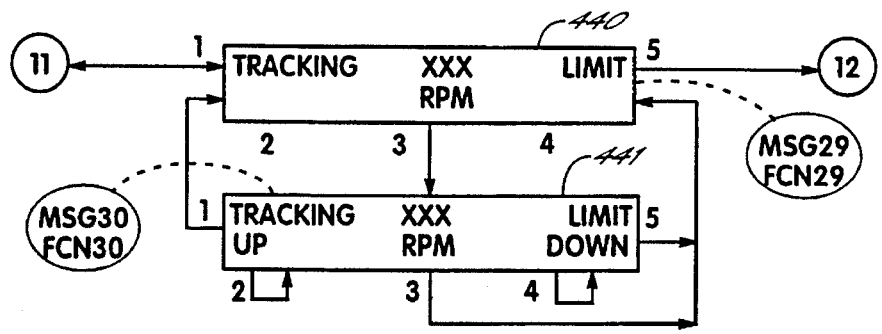

The operator may also set various other operating parameters of the console shaker through other displays. For example, by pressing key 355 in display 430 the operator may cause microprocessor 200 to proceed to display 440 (FIG. 10F). This display indicates the tracking limit for the shaker motor. The operator may adjust this tracking limit by pressing key 353 ("RPM"), causing microprocessor 200 to proceed to display 441. In display 441, the operator may increase or decrease the tracking limit by pressing keys 352 ("up") or 354 ("down"). Once the desired tracking limit has been entered, the operator may return to display 440 by pressing key 353.

Figure 10G:
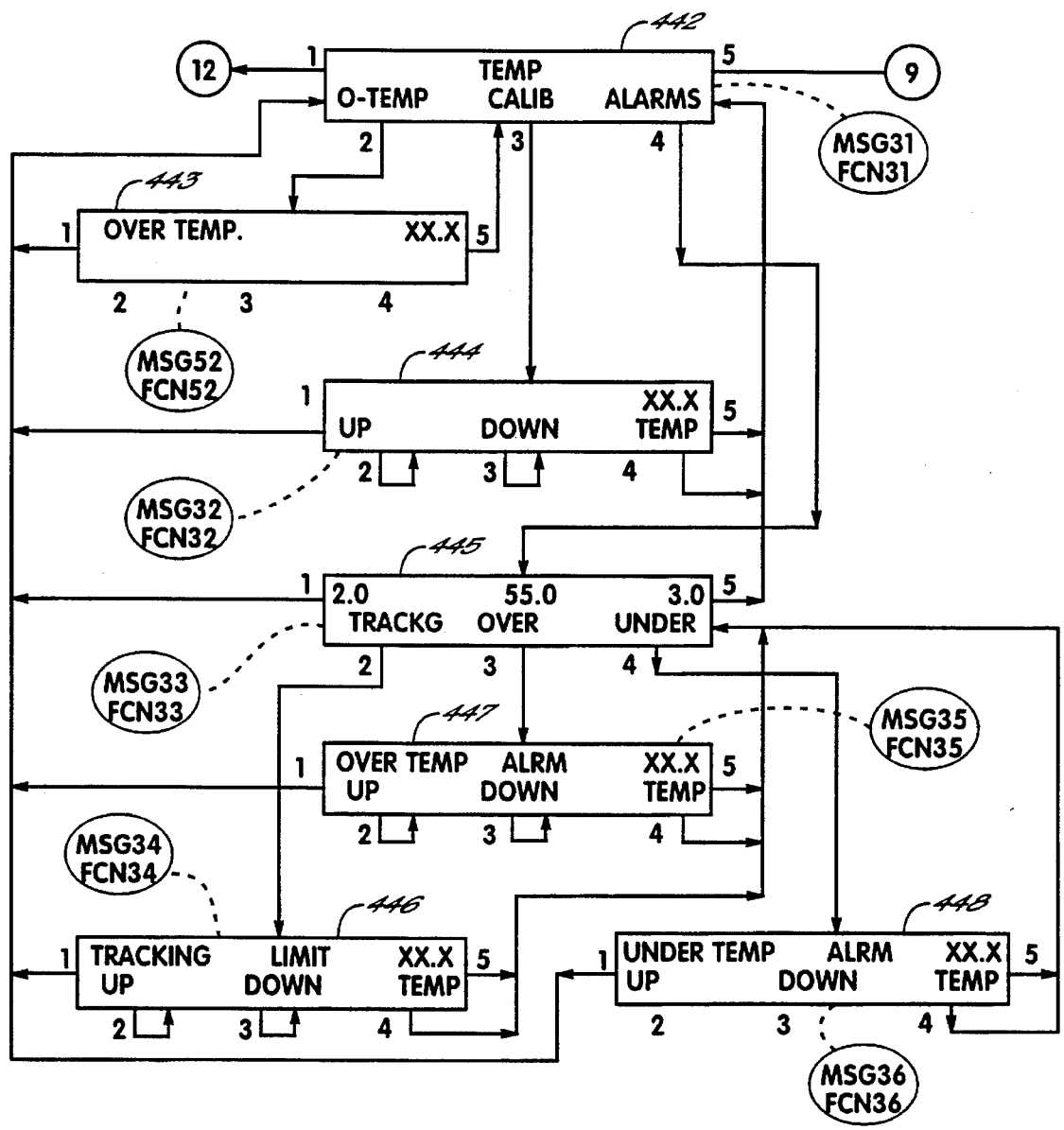

The operator may also set tracking and alarm parameters for the temperature controller functions of console shaker 100 (FIG. 1) by operations leading from display 442 (FIG. 10G). The operator may access display 442 by pressing key 355 from display 440. Display 442 identifies various temperature control functions that may adjusted by the operator.

Specifically, the operator may press key 352 ("o-temp") to move to display 443. Display 443 indicates the temperature reading being received from the secondary or over temperature sensor 260. This temperature reading can be used to determine whether the main temperature sensor is operating properly. Similarly, the operator may move from display 442 to display 444 by depressing key 353 ("temp calib"). Display 444 indicates a calibration value which may be used to adjust the factory calibration of the temperature sensor, i.e., an offset which is added or subtracted from the temperature reading produced by the temperature sensor 260. The operator may adjust this temperature calibration upward or downward to a maximum of 2° C. from the factory setting by depressing keys 352 ("up") and 353 ("down"). When the desired recalibration has been achieved, the operator may depress key 354 to return to display 442. Finally, the operator may transition from display 442 to display 445 by depressing key 354 ("alarms"). Display 445 indicates the tracking limit and over temperature and under temperature alarm thresholds used by console shaker 100 (FIG. 1). For example, as illustrated in FIG. 10G, the tracking limit alarm sounds if the temperature is more than 2° C. away from the desired set point temperature, the over temperature alarm sounds if the shaker temperature exceeds 55° C. and the under temperature alarm sounds if the shaker temperature falls below 3° C. The operator may depress key 352 ("trackg") to transition to display 446 to adjust the temperature tracking limit alarm threshold. This adjustment is performed in a similar manner to that discussed above with reference to display 444, using keys 352 ("up") and 353 ("down"). Similarly, the operator may move from display 445 to display 447 to adjust the over temperature alarm threshold by depressing key 353 in display 445 ("over"). In display 447, the operator may adjust the over temperature alarm threshold using key 352 ("up") and key 353 ("down"). Finally, the operator may move from display 445 to display 448 to adjust the under temperature alarm threshold by depressing key 354 ("under") in display 445. The under temperature alarm threshold may be adjusted in display 448 using keys 352 ("up") and 353 ("down").

Figure 10H:
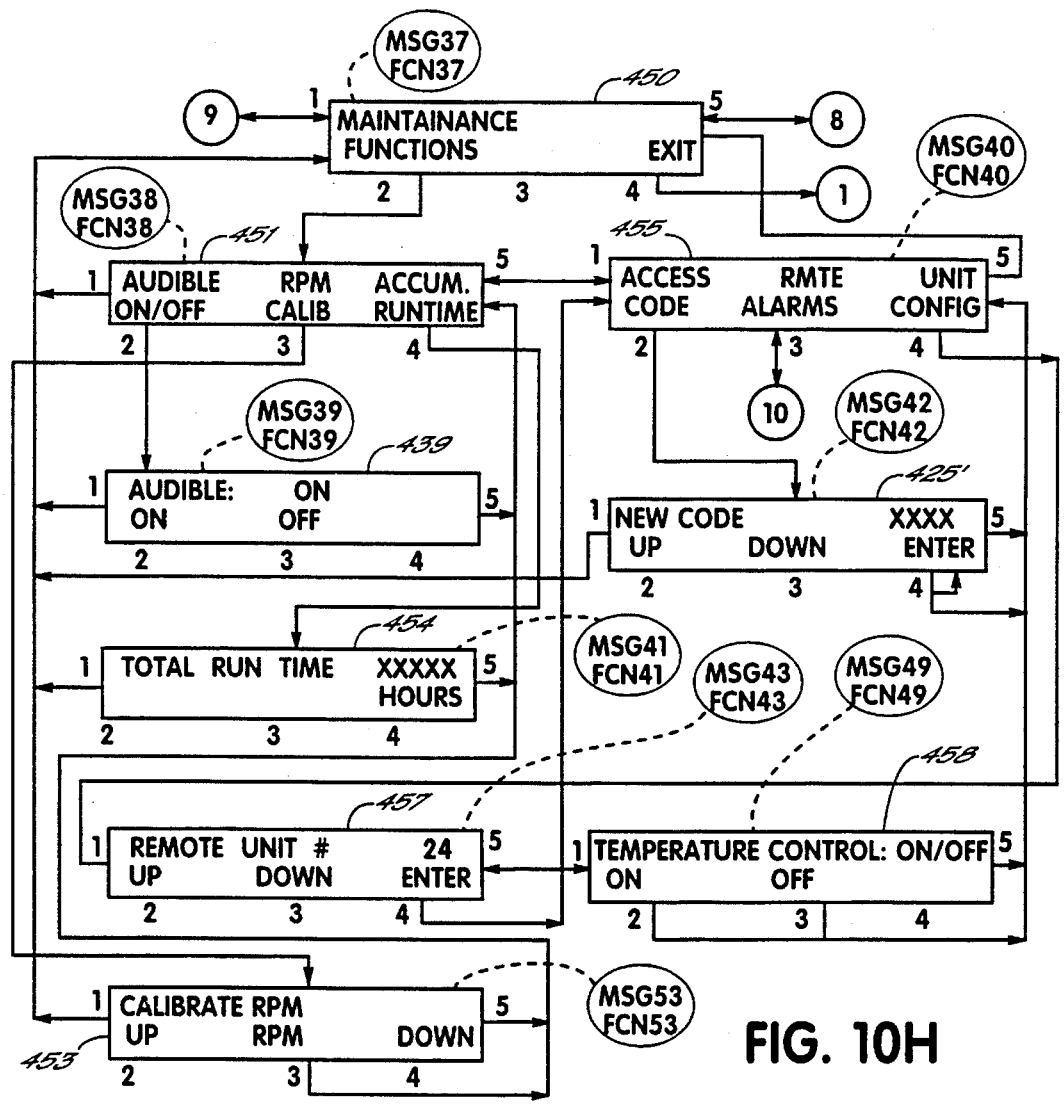
Figure 10I:
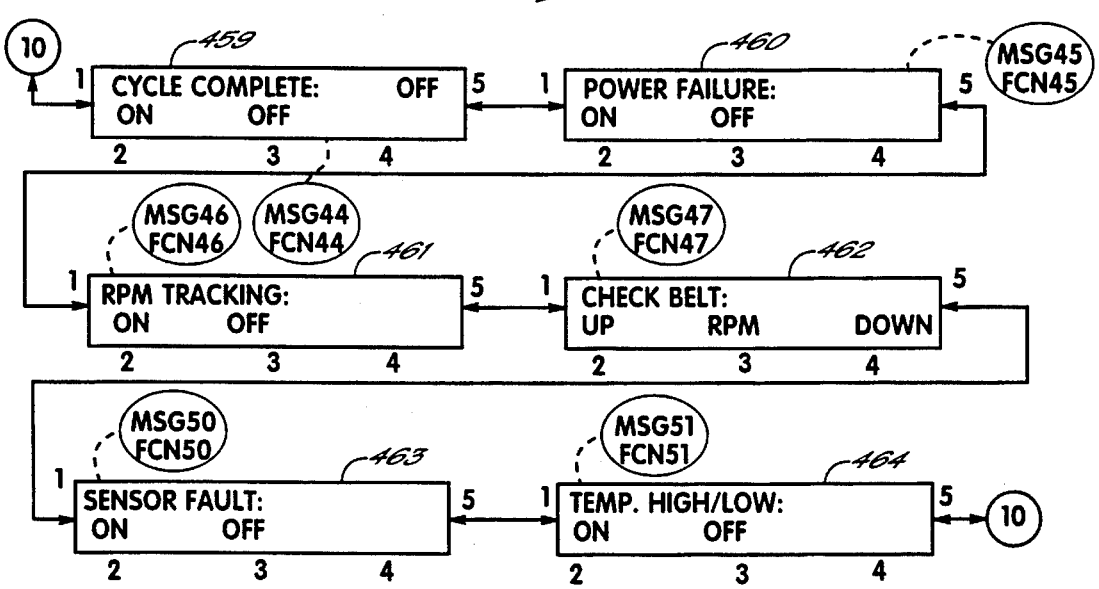

The operator may also perform additional maintenance functions by proceeding to display 450 (FIG. 10H). The operator may move to display 450 by pressing key 355 in display 442. In display 450, the operator may depress key 352 ("maintenance functions") to adjust various additional parameters of console shaker 100 (FIG. 1). Doing so transitions to display 451 through which the operator may turn the speaker and audible alarms on and off by depressing key 352 ("audible on/off") causing microprocessor 200 to transition to display 452. In addition, in display 451, the operator may recalibrate the RPM measurements by pressing key 353 ("RPM calib"), causing microprocessor 200 to transition to display 453. In this display, the operator may enter a calibration value to be added to or subtracted from the factory calibrated RPM reading. Finally, in display 451 the operator may press key 354 ("accum. runtime") to display the total accumulated runtime of the console shaker by transitioning to display 454.

The operator may also access additional functions by pressing keys 355 in display 451, thereby transitioning to display 455. Once in display 455, the operator may press key 352 ("access code") to enter a new access code by moving to display 456 (the access code is entered in manner similar to that discussed above with reference to display 403). Furthermore, the operator may configure the console shaker by pressing key 354 ("unit config"), causing microprocessor 200 to transition to display 457 in which the operator may indicate the remote unit number used for the RS-232/RS-485 interface to the console shaker, or may transition to display 458 in which the operator may indicate whether the temperature control circuit is enabled or disabled. Finally, the operator may depress 353 ("rmte alarms") in display 455, to indicate which alarm conditions are to be remotely identified through the external alarm connector 258. Doing so causes microprocessor 200 to transition through displays 459, 460, 461, 462, 463 and 464 (FIG. 10I) in which the operator can indicate whether the completion of a cycle, power failure, a shaker-motor RPM tracking failure, a shaker-motor belt failure, a temperature sensor fault or an over temperature or under temperature event, respectively, should be identified through external alarm connector 258 to a remote system.

Although a preferred embodiment of the present invention has been fully detailed above, it will be appreciated that many modifications may be made thereto without departing from the spirit and scope of the invention. Therefore, it is not Applicants' intent to be bound by the details provided but only by the scope of the appended claims.

What is claimed is:

1. A console shaker comprising:
   a chamber surrounded by insulated outside walls including front and rear outside walls and a pair of outside end walls and an upper lid;
   an air jacket disposed between said chamber and said insulated outside walls, said air jacket formed by air jacket side walls spaced inwardly from said insulated outside walls and creating front and rear air plenums between said front and rear outside walls and said chamber and supply and return air plenums between said outside end walls and said chamber, wherein said supply and return air plenums are connected to said front and rear air plenums and the air jacket side walls which are spaced from said end walls further include apertures;
   a fan disposed within an air circulation path of said air jacket for circulating air from said supply plenum to said return plenum through both said front and rear air plenums and said chamber; and,
   a shaker device disposed within said chamber.

2. The console shaker of claim 1 further comprising a refrigeration device disposed within the air circulation path of said air jacket for cooling the air circulating within said air circulation path.

3. The console shaker of claim 2 further comprising a heating device disposed within the air circulation path of said air jacket for heating the air circulating within said air circulation path.

4. The console shaker of claim 3 further comprising a microprocessor control system connected to said shaker device, said refrigeration device and said heating device for controlling shaking speed and shaking duration and controlling temperature within said chamber.

5. The console shaker of claim 4 wherein said microprocessor control system includes programmable memory for storing a plurality of preset and selectively retrievable programs, each program including a value for the shaking speed, the shaking duration and the temperature of said chamber.

6. The console shaker of claim 5 wherein said microprocessor control system is operated by a keypad mounted on a front portion of said lid.

7. The console shaker of claim 4 wherein said air jacket further includes a bottom air plenum disposed beneath said chamber, said bottom air plenum extending between said supply and return plenums and defining a further portion of said air circulation path.

8. The console shaker of claim 1 further comprising a heating device disposed within the air circulation path of said air jacket for heating the air circulating within said air circulation path.

9. The console shaker of claim 8 further comprising a temperature control compartment containing said heating device and said fan, said temperature control compartment disposed within a base of the console shaker and connected by air paths between said supply and return air plenums, wherein said air jacket further includes a bottom air plenum located between said chamber and said temperature control compartment, said bottom air plenum extending between said supply and return plenums and defining a further portion of said air circulation path.

10. The console shaker of claim 9 further comprising a high efficiency particulate air filter mounted within said air circulation path.

11. The console shaker of claim 10 wherein said high efficiency particulate air filter is mounted adjacent the air jacket side wall of said air supply plenum.

12. The console shaker of claim 1 further comprising a high efficiency particulate air filter mounted within said air circulation path.

13. The console shaker of claim 12 wherein said high efficiency particulate air filter is mounted adjacent the air jacket side wall of said air supply plenum.

14. The console shaker of claim 13 wherein said air jacket further includes a bottom air plenum disposed beneath said chamber, said bottom air plenum extending between said supply and return plenums and defining a further portion of said air circulation path.

15. The console shaker of claim 1 wherein said air jacket walls are part of an air jacket insert, and said insert further includes top walls extending between said air jacket side walls and said insulated outside walls.

16. The console shaker of claim 1 further including a plurality of lights disposed on an underside of said lid.

17. The console shaker of claim 1 wherein said shaker device is an orbital shaker having an orbiting mechanism located below said chamber and an orbiting platform located within said chamber.

18. The console shaker of claim 1 further comprising a microprocessor control system connected to said shaker device for controlling shaking speed and duration.

19. A console shaker comprising:
   a chamber surrounded by insulated outside walls including front and rear outside walls and a pair of outside end walls and an upper lid;
   an air jacket disposed between said chamber and said insulated outside walls, said air jacket formed by air jacket side walls spaced inwardly from said insulated outside walls and creating front and rear air plenums between said front and rear outside walls and said chamber and supply and return air plenums between said outside end walls and said chamber, said air jacket further including a bottom air plenum located beneath and adjacent to a bottom of said chamber, wherein said supply and return air plenums are connected to said front, rear and bottom air plenums and the air jacket side walls which are spaced from said end walls further include apertures;
   a fan disposed within an air circulation path of said air jacket for circulating air from said supply plenum to said return plenum through said front, rear and bottom air plenums and said chamber; and,
   a shaker device disposed within said chamber.

20. The console shaker of claim 19 further comprising a refrigeration device disposed within the air circulation path of said air jacket for cooling the air circulating within said air circulation path.

21. The console shaker of claim 20 further comprising a microprocessor control system connected to said shaker device and said refrigeration device for controlling shaking speed and shaking duration and controlling temperature within said chamber.

22. The console shaker of claim 21 wherein said microprocessor control system includes programmable memory for storing a plurality of preset and selectively retrievable programs, each program including a value for the shaking speed, the shaking duration and the temperature of said chamber.

23. The console shaker of claim 22 wherein said microprocessor control system is operated by a keypad mounted on a front portion of said lid.

24. The console shaker of claim 19 further comprising a heating device disposed within the air circulation path of said air jacket for heating the air circulating within said air circulation path.

25. The console shaker of claim 24 further comprising a microprocessor control system connected to said shaker device and said heating device for controlling shaking speed and shaking duration and controlling temperature within said chamber.

26. The console shaker of claim 25 wherein said microprocessor control system includes programmable memory for storing a plurality of preset and selectively retrievable programs, each program including a value for the shaking speed, the shaking duration and the temperature of said chamber.

27. The console shaker of claim 26 wherein said microprocessor control system is operated by a keypad mounted on a front portion of said lid.

28. The console shaker of claim 19 further comprising a temperature regulating device located in a compartment disposed within a base of the console shaker and connected by air paths between said supply and return air plenums, wherein said bottom air plenum is located between the bottom of said chamber and a top of said compartment.

29. The console shaker of claim 28 further comprising a high efficiency particulate air filter mounted within said air circulation path.

30. The console shaker of claim 29 wherein said high efficiency particulate air filter is mounted adjacent the air jacket side wall of said air supply plenum.

31. The console shaker of claim 19 further comprising a high efficiency particulate air filter mounted within said air circulation path.

32. The console shaker of claim 19 wherein said air jacket walls are part of an air jacket insert, and said insert further includes top walls extending between said air jacket side walls and said insulated outside walls.

33. The console shaker of claim 19 further including a plurality of lights disposed on an underside of said lid.

34. The console shaker of claim 19 wherein said shaker device is an orbital shaker having an orbiting mechanism located below said chamber and an orbiting platform located within said chamber.

35. A console shaker comprising:
- an insulated chamber having plurality of side walls, a bottom and an upper lid;
- a shaker device disposed within said chamber;
- first and second temperature sensors monitoring the temperature of said chamber;
- a temperature regulating device responsive to said first and second temperature sensors and connected with said chamber for regulating the temperature thereof; and,
- a microprocessor control connected to both said shaker device and said temperature regulating device for controlling shaking speed and shaking duration and controlling the operation of said temperature regulating device to control the temperature within said chamber.

36. The console shaker of claim 35 wherein said temperature sensors comprise temperature sensitive electrical elements producing first and second analog electrical temperature signals respectively related to temperature detected by said first and second temperature sensors.

37. The console shaker of claim 36 wherein said temperature regulating element comprises
- an analog-to-digital converter connected to said temperature sensors for converting said first and second analog electrical temperature signals to digital signals;
- a linearization circuit for linearizing digital signals from said analog-to-digital converter to produce first and second digital temperature signals linearly related to detected temperature and deliver said digital temperature signals to said microprocessor control; and
- a heating element;
- wherein said microprocessor activates said heating element in response to detected temperature of said chamber based on one or both of said digital temperature signals.

38. The console shaker of claim 37 wherein said microprocessor control compares said first and second digital temperature signals to confirm proper operation of said first and second temperature sensitive electrical elements, and said microprocessor control activates said heating element only when proper operation of said first and second temperature sensitive electrical elements has been confirmed.

39. The console shaker of claim 37 wherein said temperature regulating element further comprises a refrigerating element, wherein said microprocessor control activates said refrigerating element in response to detected temperature of said chamber based on one or both of said digital temperature signals.

40. The console shaker of claim 36 further comprising
- a first threshold generating circuit producing a first analog electrical threshold signal;
- a first comparison circuit for comparing said first analog electrical threshold signal to said first analog electrical temperature signal, and asserting a first hardware alarm signal when said first analog electrical temperature signal has a predetermined relationship to said first analog electrical threshold signal;
- wherein said temperature regulating element is responsive to said first hardware alarm signal for deactivating said temperature regulating element upon assertion of said first hardware alarm signal.

41. The console shaker of claim 40 further comprising
- a second threshold generating circuit producing a second analog electrical threshold signal;
- a second comparison circuit for comparing said second analog electrical threshold signal to said first analog electrical temperature signal, and asserting a second hardware alarm signal when said first analog electrical temperature signal has a predetermined relationship to said second analog electrical threshold signal;
- wherein said temperature regulating element is further responsive to said second hardware alarm signal for deactivating said temperature regulating element upon assertion of said second hardware alarm signal.

42. The console shaker of claim 40 wherein said temperature regulating element comprises
- an analog-to-digital converter connected to said first temperature sensor and said first threshold generating circuit for converting said first analog electrical temperature signal and said first analog electrical threshold signal to digital signals and forwarding said digital signals toward said microprocessor control;

wherein said first hardware alarm signal is also delivered to said microprocessor control so that said microprocessor control may confirm proper operation of said first threshold generating circuit and said first comparison circuit, said microprocessor control confirming proper operation by determining whether a digital signal generated from said first analog electrical temperature signal has said predetermined relationship to a digital signal generated from said first analog electrical threshold signal, and if so, determining whether said first hardware alarm signal has been asserted.

43. The console shaker of claim 35 further comprising a display connected to said microprocessor control, said microprocessor control controlling said display to display information regarding the shaking speed, the shaking duration or the temperature of said chamber; and a keypad connected to said microprocessor control, said microprocessor control being responsive to operator actuation of keys on said keypad to control operations of said console shaker and said display.

44. The console shaker of claim 43 wherein said microprocessor control has at least a first and a second operating mode, at least one key on said keypad is a multi-functional key which may be used to initiate one a first operation of said console shaker upon operator actuation thereof while said microprocessor control is in said first operating mode, and may be used to initiate a second different operation of said console shaker upon operator actuation thereof while said microprocessor control is in said second operating mode, said multi-functional key is located physically adjacent to a indicating region of said display, and in said first operating mode said microprocessor control causes said display to display, in said indicating region, information identifying said first operation, and in said second operating mode said microprocessor control causes said display to display, in said indicating region, information identifying said second operation.

45. The console shaker of claim 35 further comprising a keypad connected to said microprocessor control, said microprocessor control being responsive to operator actuation of keys on said keypad to identify a calibration factor to be used by said microprocessor control in controlling said console shaker.

46. The console shaker of claim 45 wherein said calibration value is an offset to be added to temperature readings obtained from a said temperature sensor.

47. The console shaker of claim 45 further comprising a RPM sensor connected to said microprocessor control for reading a shaking speed to be used in controlling said shaker device, wherein said calibration value is an offset to be added to RPM readings obtained from said RPM sensor.

48. The console shaker of claim 35 further comprising an external interface port connected to said microprocessor control, said microprocessor control generating an electrical signal to said external interface port indicative of shaking speed, the shaking duration or the temperature of said chamber.

49. The console shaker of claim 48 wherein said microprocessor control generates said electrical signals to said external interface port in accordance with a preset schedule.

50. The console shaker of claim 48 wherein said microprocessor control is responsive to electrical signals from said external interface port to generate said electrical signals to said external interface port.

51. The console shaker of claim 35 further comprising an external alarm connector having two terminals, and a switch connected to said microprocessor control, said microprocessor indicating the presence or absence of an alarm condition by moving said switch between a position at which said switch creates an electrical connection between said terminals, and a position at which said switch does not create an electrical connection between said terminals.

52. A console shaker comprising:

an insulated chamber having plurality of side walls, a bottom and an upper lid;

a shaker device disposed within said chamber;

a temperature regulating device connected with said chamber for regulating the temperature thereof; and, a microprocessor control connected to both said shaker device and said temperature regulating device for controlling shaking speed and shaking duration and controlling the operation of said temperature regulating device to control the temperature within said chamber, wherein said microprocessor control includes programmable memory for storing a plurality of preset and selectively retrievable programs, each program including a value for the shaking speed, the shaking duration and the temperature of said chamber.

53. The console shaker of claim 52 further comprising a keypad connected to said microprocessor control, said microprocessor control being responsive to operator actuation of keys of said keypad to select one of said selectively retrievable programs.

54. The console shaker of claim 53 wherein said microprocessor control is responsive to operator actuation of keys of said keypad to alter one of said selectively retrievable programs.

55. The console shaker of claim 53 wherein said microprocessor control is responsive to operator actuation of keys of said keypad to alter one of said selectively retrievable programs only after receipt of an access code through operator actuation of keys on said keypad.

56. A console shaker comprising:

an insulated chamber having plurality of side walls, a bottom and an upper lid;

a shaker device disposed within said chamber;

a temperature sensor connected with said chamber for monitoring the temperature of said chamber;

a temperature alarm circuit connected to said temperature sensor for detecting temperatures of said chamber outside of a desirable range and asserting a hardware alarm signal upon detection of a temperature outside of said desirable range;

a temperature regulating device connected with said chamber for regulating the temperature thereof, said temperature regulating device being responsive to said hardware alarm signal to deactivate said temperature regulating device upon assertion of said hardware alarm signal; and a microprocessor control connected to said shaker device, said temperature sensor and said temperature regulating device for controlling shaking speed and shaking duration, and controlling operation of said temperature regulating device in response to temperature readings from said temperature sensor to control the temperature within said chamber.

57. The console shaker of claim 56 wherein said temperature sensor comprises a temperature sensitive electrical element producing a first analog electrical temperature signal related to temperature detected by said temperature sensor.

58. The console shaker of claim 57 wherein said temperature alarm circuit comprises a first threshold generating circuit producing a first analog electrical threshold signal;

a first comparison circuit for comparing said first analog electrical threshold signal to said first analog electrical temperature signal, and asserting said hardware alarm signal when said first analog electrical temperature signal has a predetermined relationship to said first analog electrical threshold signal.

59. The console shaker of claim 58 further comprising a second temperature alarm circuit comprising a second threshold generating circuit producing a second analog electrical threshold signal;

a second comparison circuit for comparing said second analog electrical threshold signal to said first analog electrical temperature signal, and asserting a second hardware alarm signal when said first analog electrical temperature signal has a predetermined relationship to said second analog electrical threshold signal;

wherein said temperature regulating element is further responsive to said second hardware alarm signal for deactivating said temperature regulating element upon assertion of said second hardware alarm signal.

60. The console shaker of claim 58 wherein said temperature regulating element comprises an analog-to-digital converter connected to said temperature sensor and said first threshold generating circuit for converting said first analog electrical temperature signal and said first analog electrical threshold signal to digital signals and forwarding said digital signals toward said microprocessor control;

wherein said hardware alarm signal is also delivered to said microprocessor control so that said microprocessor control may confirm proper operation of said first threshold generating circuit and said first comparison circuit, said microprocessor control confirming proper operation by determining whether a digital signal generated from said first analog electrical temperature signal has said predetermined relationship to a digital signal generated from said first analog electrical threshold signal, and if so, determining whether said hardware alarm signal has been asserted.

61. The console shaker of claim 56 further comprising an additional temperature sensor connected with said chamber for monitoring the temperature of said chamber;

wherein said microprocessor control is further connected to said additional temperature sensor, compares temperature readings from said temperature sensors to confirm proper operation of said temperature sensors, and activates said temperature regulating element only when proper operation of said temperature sensors has been confirmed.

62. The console shaker of claim 56 further comprising a keypad connected to said microprocessor control, said microprocessor control being responsive to operator actuation of keys on said keypad to identify a calibration factor to be applied to temperature readings from said temperature sensor and used by said microprocessor control in controlling said temperature regulating element.

\* \* \* \* \*